(12) United States Patent
Brown et al.

(10) Patent No.: US 12,162,921 B2
(45) Date of Patent: Dec. 10, 2024

(54) INVERTED TRANSPORTER POLYPEPTIDES AND METHODS OF USING

(71) Applicant: Howard Hughes Medical Institute, Chevy Chase, MD (US)

(72) Inventors: Jennifer Brown, Ashburn, VA (US); Reza Behnam, Ashburn, VA (US); Luke Coddington, Ashburn, VA (US); Dougal Gowanlock Robinson Tervo, Ashburn, VA (US); Joshua Dudman, Leesburg, VA (US); Alla Karpova, Ashburn, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 848 days.

(21) Appl. No.: 16/972,316

(22) PCT Filed: Jun. 4, 2019

(86) PCT No.: PCT/US2019/035344
§ 371 (c)(1),
(2) Date: Dec. 4, 2020

(87) PCT Pub. No.: WO2019/236547
PCT Pub. Date: Dec. 12, 2019

(65) Prior Publication Data
US 2021/0246185 A1    Aug. 12, 2021

Related U.S. Application Data

(60) Provisional application No. 62/680,130, filed on Jun. 4, 2018.

(51) Int. Cl.
C07K 14/705    (2006.01)
C12N 15/86    (2006.01)

(52) U.S. Cl.
CPC .......... *C07K 14/705* (2013.01); *C12N 15/86* (2013.01); *C07K 2319/02* (2013.01); *C07K 2319/03* (2013.01); *C12N 2750/14143* (2013.01)

(58) Field of Classification Search
CPC .............. C07K 14/705; C07K 2319/02; C07K 2319/03; C12N 15/86; C12N 2750/14143; C12N 15/52
See application file for complete search history.

(56) References Cited

U.S. PATENT DOCUMENTS

2014/0356896 A1    12/2014    Frommer et al.

FOREIGN PATENT DOCUMENTS

| WO | WO2002/31109 | 4/2002 |
|---|---|---|
| WO | WO2005/017149 | 2/2005 |
| WO | WO2011/005978 | 1/2011 |
| WO | WO2016/149274 | 9/2016 |

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Berndt et al., "Structure-Guided Transformation of Channelrhodopsin into a Light-Activated Chloride Channel," Science, Apr. 25, 2014, 344:420-424.
Brown et al., "Expanding the Optogenetics Toolkit by Topological Inversion of Rhodopsins," Cell, Oct. 18, 2018, vol. 175, pp. 1131-1140.
Brown et al., "The inhibitory microcircuit of the substantia nigra provides feedback gain control of the basal ganglia output," eLife, 3:e02397, May 21, 2014, 25 pages.
Gadsby, David C., "Ion channels versus ion pumps: the principal difference, in principle," Nature Reviews Molecular Cell Biology, Apr. 2, 2009, 10:344-352.
Gallivan et al., "Three-dimensional reach trajectories as a probe of real-time decision-making between multiple competing targets," *Front. Neurosci.*, Jul. 23, 2014, 8:215.
Guo et al., "Single-axon level morphological analysis of corticofugal projection neurons in mouse barrel field," Scientific Reports, 7: 2846, Jun. 6, 2017, 9 pages.
Karlsson et al., "Network Resets in Medial Prefrontal Cortex Mark the Onset of Behavioral Uncertainty," Science, Oct. 5, 2012, vol. 338, Issue 6103, pp. 135-139.
Lima et al., "PINP: A New Method of Tagging Neuronal Populations for Identification during In Vivo Electrophysiological Recording," PLoS One 4(7): e6099, Jul. 7, 2009, 10 pages, https://doi.org/10.1371/journal.pone.0006099.
Osborne et al., "RIVETS: A Mechanical System for In Vivo and In Vitro Electrophysiology and Imaging," PLoS One 9(2): e89007, Feb. 14, 2014, 10 pages, https://doi.org/10.1371/journal.pone.0089007.
Panigrahi et al., "Dopamine Is Required for the Neural Representation and Control of Movement Vigor," Cell, Sep. 10, 2015, 162(6):1418-1430.

(Continued)

*Primary Examiner* — Iqbal H Chowdhury
(74) *Attorney, Agent, or Firm* — Fish & Richardson P.C.

(57) ABSTRACT

This document provides methods and materials for modulating one or more properties of transporter proteins. For example, inverted transporter polypeptides including a leader sequence fused to a transporter protein, and methods of using one or more inverted transporter polypeptides to modulate (e.g., stimulate or inhibit) the excitability of one or more cells (e.g., neurons and myocytes) are provided.

8 Claims, 19 Drawing Sheets

Specification includes a Sequence Listing.

(56) References Cited

OTHER PUBLICATIONS

PCT International Preliminary Report on Patentability in International Application No. PCT/US2019/035344, dated Dec. 8, 2020, 9 pages.
PCT International Search Report and Written Opinion in International Application No. PCT/US2019/035344, dated Sep. 3, 2019, 12 pages.
Wang et al., "A Light- And Calcium-Gated Transcription Factor for Imaging and Manipulating Activated Neurons," Nature Biotechnology, Jun. 26, 2017, vol. 35, No. 9, pp. 1-34.
Nagel et al., "Channelrhodopsin-2, a directly light-gated cation-selective membrane channel," Proceedings of the National Academy of Sciences, Nov. 25, 2003, 100:13940-13945.
Schwiening and Boron, "Regulation of intracellular pH in pyramidal neurones from the rat hippocampus by Na +-dependent CI—$HCO_3$-exchange," The Journal of Physiology, Feb. 15, 1994, 475:59-67.

\* cited by examiner

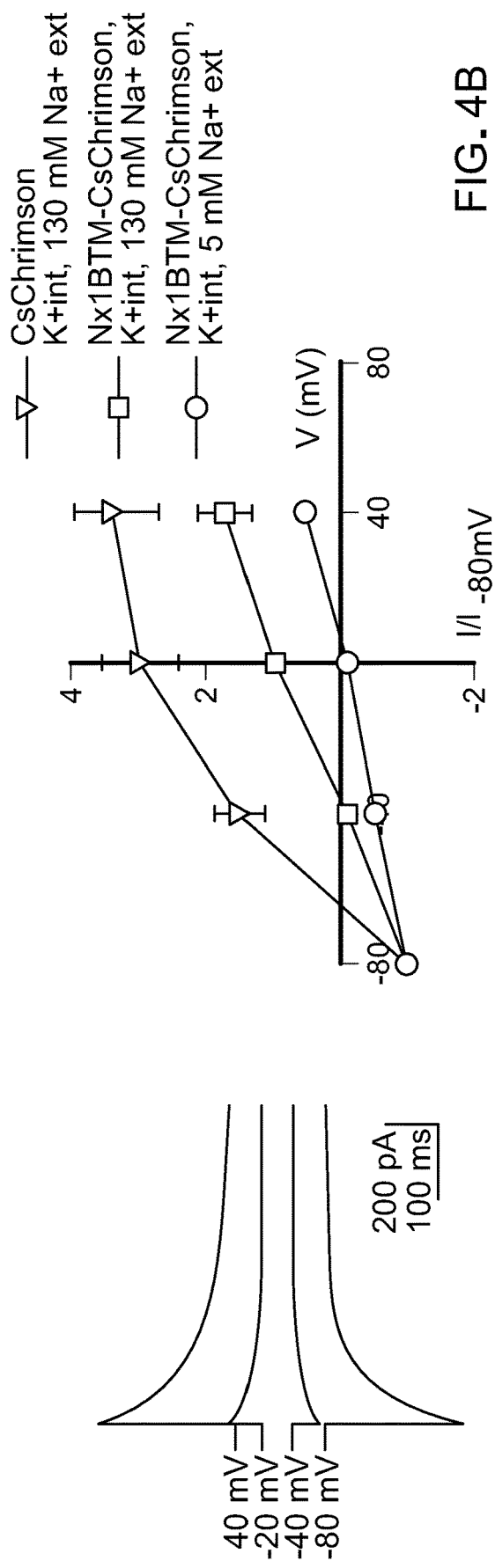
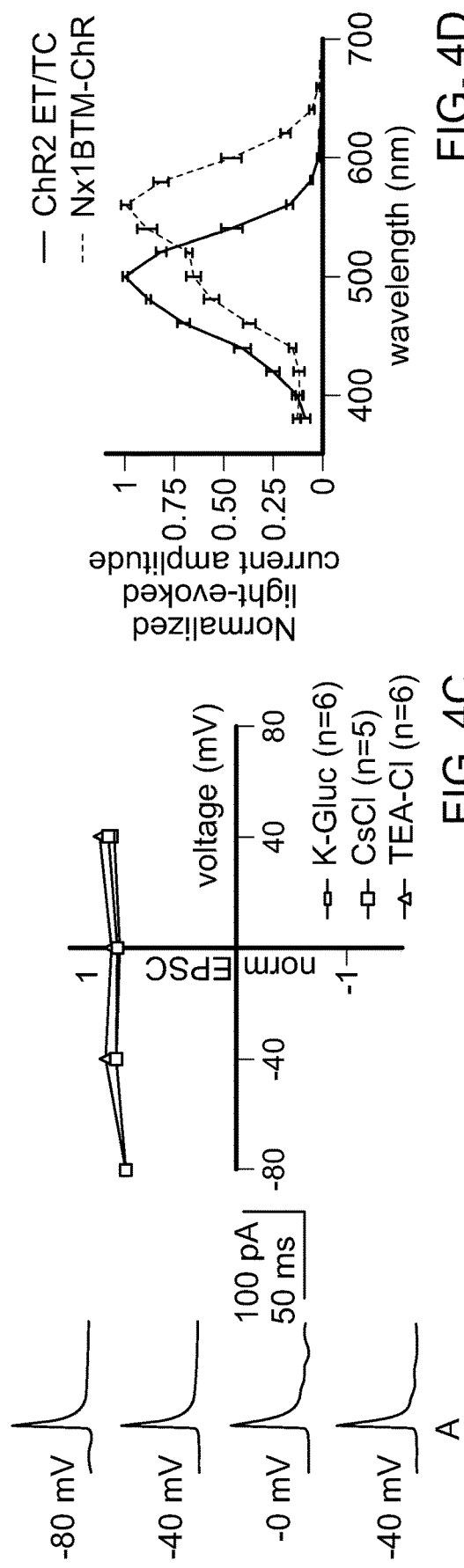
FIG. 4B
FIG. 4C
FIG. 4D

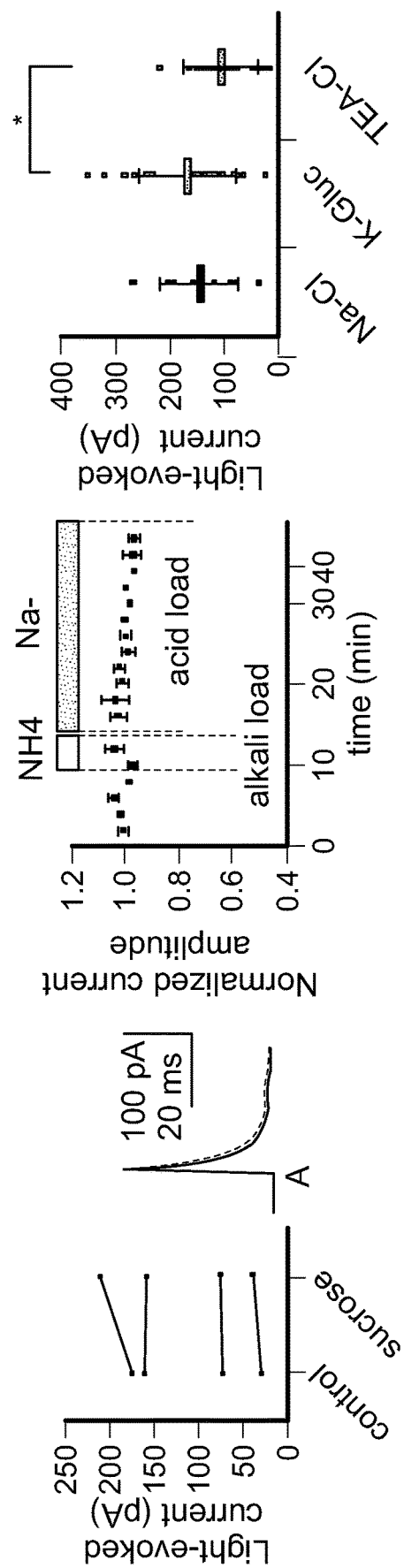

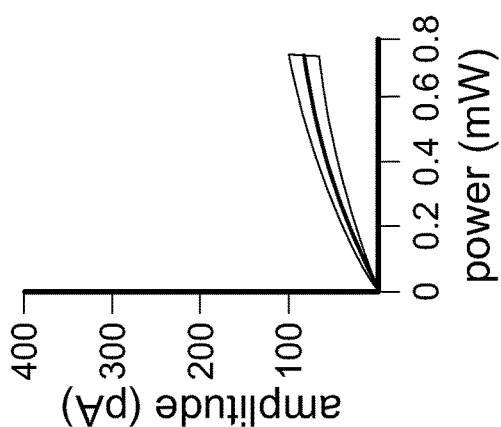
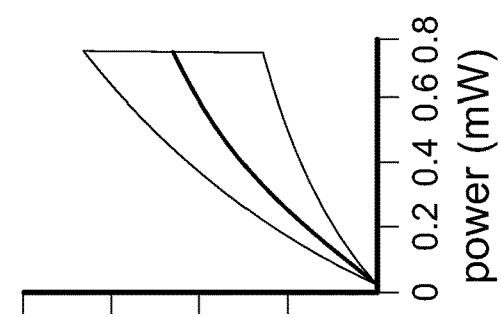
FIG. 5C
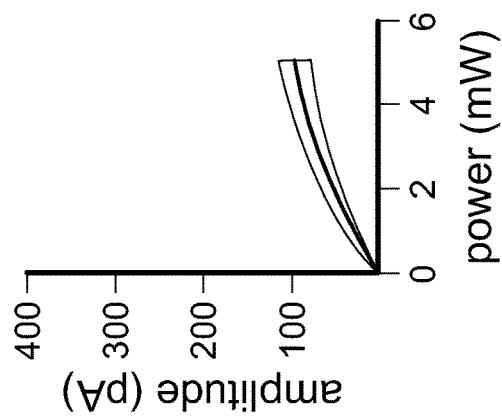
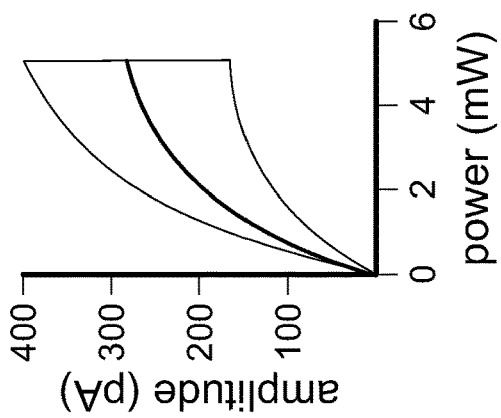
FIG. 5D
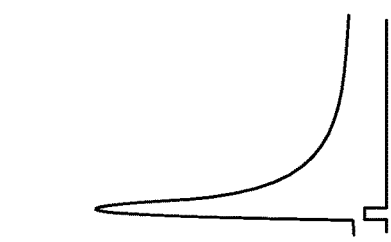
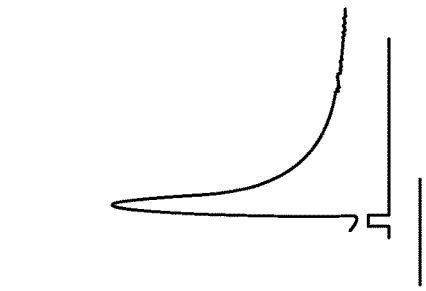
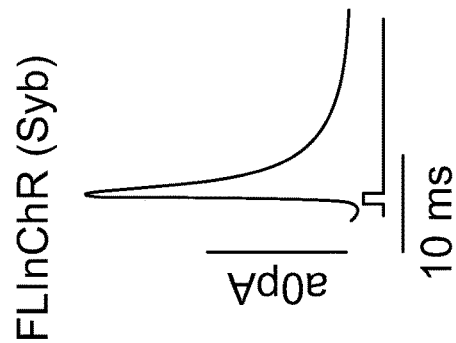
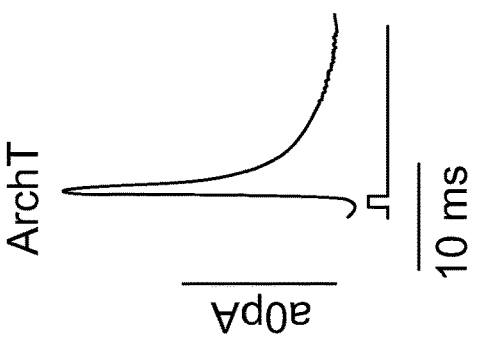

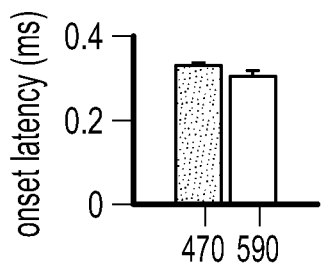
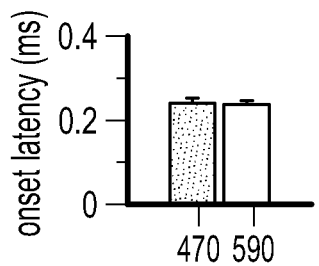
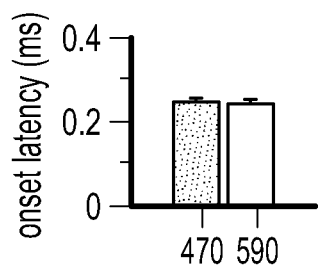
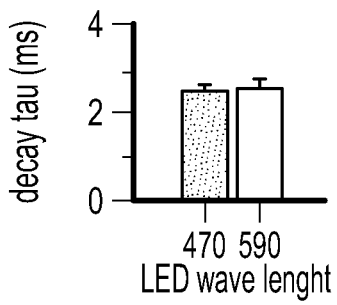
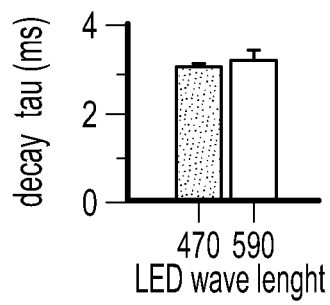
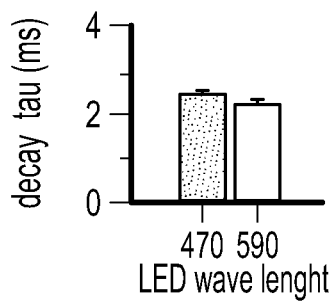
FIG. 5E    FIG. 5F    FIG. 5G
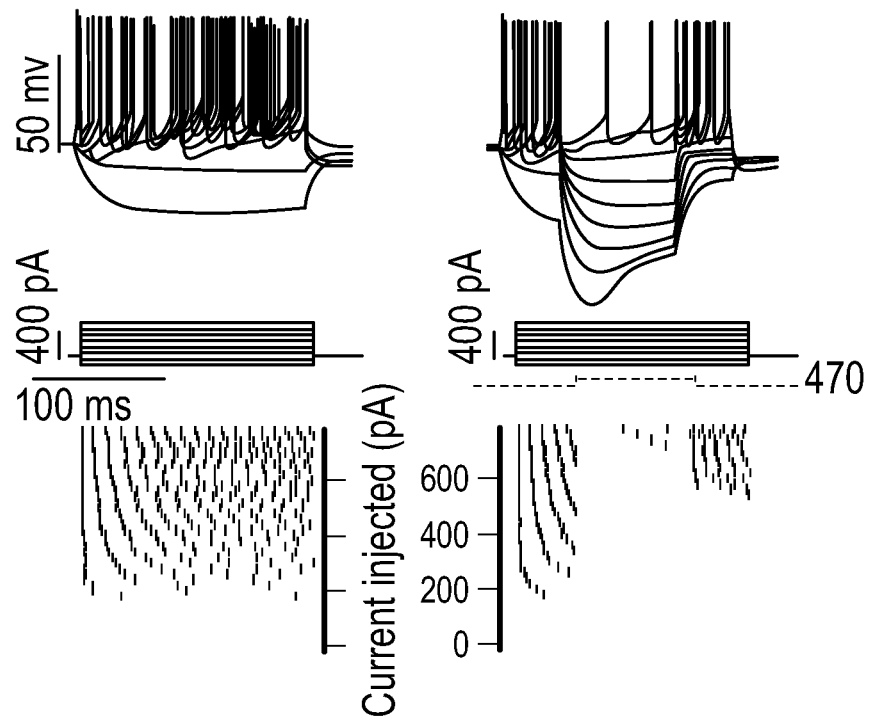
FIG. 6A

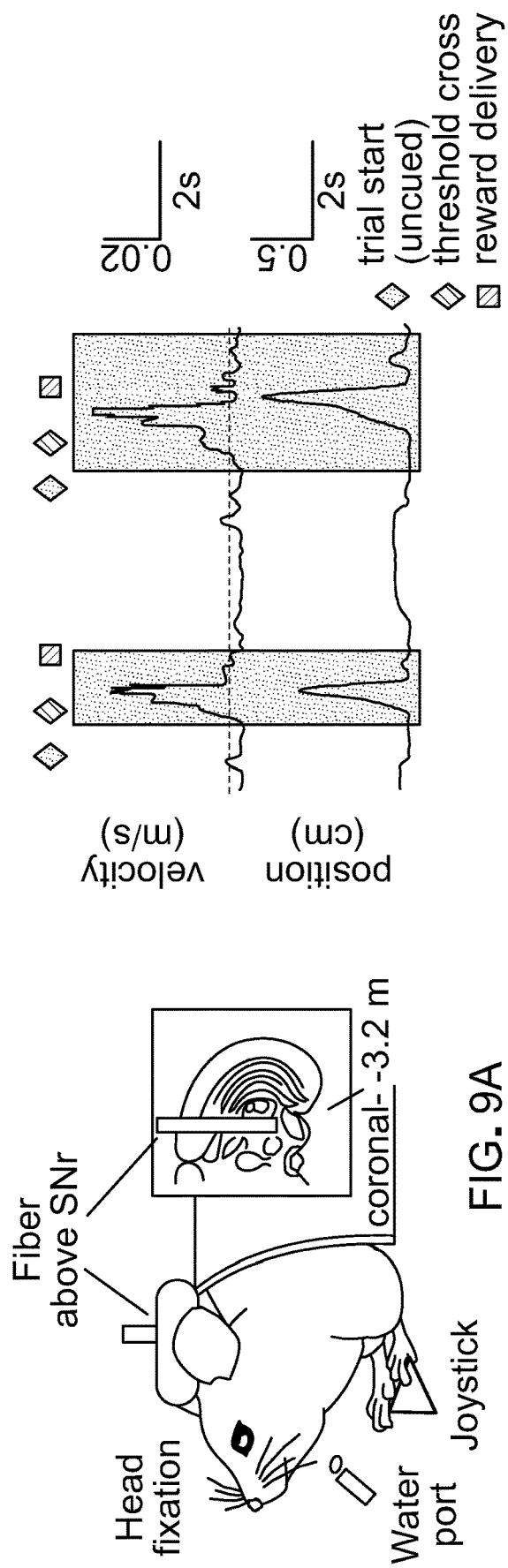
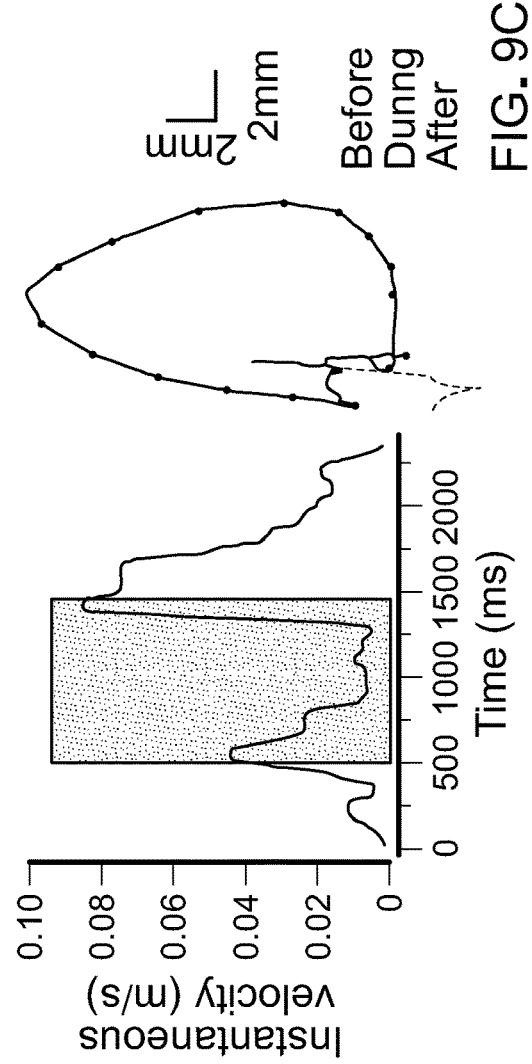
FIG. 9A
FIG. 9B
FIG. 9C

SEQUENCE LISTING

```
<160> NUMBER OF SEQ ID NOS: 7

<210> SEQ ID NO 1
<211> LENGTH: 309
<212> TYPE: PRT
<213> ORGANISM: Chlamydomonas reinhardtii

<400> SEQUENCE: 1

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
```

```
            210                 215                 220
Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
                290                 295                 300

Glu Ala Gly Ala Val
305

<210> SEQ ID NO 2
<211> LENGTH: 345
<212> TYPE: PRT
<213> ORGANISM: artificial
<220> FEATURE:
<223> OTHER INFORMATION: synthetic CsChrimson construct

<400> SEQUENCE: 2

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
                20                  25                  30

Thr Asp Gly Thr Ala Ala Ala Val Ser His Tyr Ala Met Asn Gly
                35                  40                  45

Phe Asp Glu Leu Ala Lys Gly Ala Val Val Pro Glu Asp His Phe Val
50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
                100                 105                 110

Lys Ala Thr Cys Gly Trp Glu Glu Val Tyr Val Cys Cys Val Glu Val
                115                 120                 125

Leu Phe Val Thr Leu Glu Ile Phe Lys Glu Phe Ser Ser Pro Ala Thr
130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
                180                 185                 190

Cys Val Gly Met Ile Val Phe Gly Met Ala Ala Gly Leu Ala Thr Asp
                195                 200                 205

Trp Leu Lys Trp Leu Leu Tyr Ile Val Ser Cys Ile Tyr Gly Gly Tyr
210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
```

```
                    260                 265                 270
Gly Leu Leu Lys Leu Ser Pro Tyr Ala Asn Ser Ile Gly His Ser Ile
            275                 280                 285

Cys Asp Ile Ile Ala Lys Glu Phe Trp Thr Phe Leu Ala His His Leu
        290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Phe
                325                 330                 335

Val Glu Glu Glu Asp Glu Asp Thr Val
            340                 345

<210> SEQ ID NO 3
<211> LENGTH: 152
<212> TYPE: PRT
<213> ORGANISM: artificial
<220> FEATURE:
<223> OTHER INFORMATION: leader sequence

<400> SEQUENCE: 3

Met Tyr Gln Arg Met Leu Arg Cys Gly Ala Glu Leu Gly Ser Pro Gly
1               5                   10                  15

Gly Gly Ser Ser Gly Gly Ala Gly Gly Arg Leu Ala Leu Leu Trp Ile
            20                  25                  30

Val Pro Leu Thr Leu Ser Gly Leu Leu Gly Val Ala Trp Gly Ala Ser
        35                  40                  45

Ser Leu Gly Ala His His Ile His His Lys Leu Glu Gln Lys Leu Ile
    50                  55                  60

Ser Glu Glu Asp Leu Gly Gly Leu Ala Asn Pro Thr Arg Val Gly Gly
65                  70                  75                  80

Arg Glu Pro Tyr Pro Gly Ser Ala Glu Val Ile Arg Glu Ser Ser Ser
                85                  90                  95

Thr Thr Gly Met Val Val Gly Ile Val Ala Ala Ala Leu Cys Ile
            100                 105                 110

Leu Ile Leu Leu Tyr Ala Met Lys Lys Arg Arg Ala Lys Gly Gly Ser
        115                 120                 125

Gly Gly Ser Gly Gly Leu Glu His Gly Thr Ile Pro Phe Asn Arg Thr
    130                 135                 140

His Arg Ser Lys Arg Ser Ser Gly
145                 150

<210> SEQ ID NO 4
<211> LENGTH: 393
<212> TYPE: PRT
<213> ORGANISM: artificial
<220> FEATURE:
<223> OTHER INFORMATION: leader sequence

<400> SEQUENCE: 4

Met Ser Ala Thr Ala Ala Thr Val Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60
```

```
Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                 85                  90                  95

Ile Ile Leu Gly Val Ile Cys Ala Ile Ile Leu Ile Ile Ile Ile Val
            100                 105                 110

Tyr Phe Ser Thr Gly Ser Gly Gly Ser Arg Gly Val Gln Val Glu
        115                 120                 125

Thr Ile Ser Pro Gly Asp Gly Arg Thr Phe Pro Lys Arg Gly Gln Thr
    130                 135                 140

Cys Val Val His Tyr Thr Gly Met Leu Glu Asp Gly Lys Lys Val Asp
145                 150                 155                 160

Ser Ser Arg Asp Arg Asn Lys Pro Phe Lys Phe Met Leu Gly Lys Gln
                165                 170                 175

Glu Val Ile Arg Gly Trp Glu Glu Gly Val Ala Gln Met Ser Val Gly
            180                 185                 190

Gln Arg Ala Lys Leu Thr Ile Ser Pro Asp Tyr Ala Tyr Gly Ala Thr
        195                 200                 205

Gly His Pro Gly Ile Ile Pro Pro His Ala Thr Leu Val Phe Asp Val
    210                 215                 220

Glu Leu Leu Lys Leu Glu Thr Arg Gly Val Gln Val Glu Thr Ile Ser
225                 230                 235                 240

Pro Gly Asp Gly Arg Thr Phe Pro Lys Arg Gly Gln Thr Cys Val Val
                245                 250                 255

His Tyr Thr Gly Met Leu Glu Asp Gly Lys Lys Val Asp Ser Ser Arg
            260                 265                 270

Asp Arg Asn Lys Pro Phe Lys Phe Met Leu Gly Lys Gln Glu Val Ile
        275                 280                 285

Arg Gly Trp Glu Glu Gly Val Ala Gln Met Ser Val Gly Gln Arg Ala
    290                 295                 300

Lys Leu Thr Ile Ser Pro Asp Tyr Ala Tyr Gly Ala Thr Gly His Pro
305                 310                 315                 320

Gly Ile Ile Pro Pro His Ala Thr Leu Val Phe Asp Val Glu Leu Leu
                325                 330                 335

Lys Leu Glu Ser Ala Glu Gln Lys Ile Ser Glu Glu Asp Lys Glu Gln
            340                 345                 350

Lys Ile Ser Glu Glu Asp Lys Gly Thr Ser Ala Arg Asn Arg Gln Lys
        355                 360                 365

Arg Ala Ser Gly Thr Gly Arg Gly Ser Leu Leu Thr Cys Gly Asp
    370                 375                 380

Val Glu Glu Asn Pro Gly Pro Ser Gly
385                 390

<210> SEQ ID NO 5
<211> LENGTH: 707
<212> TYPE: PRT
<213> ORGANISM: artificial
<220> FEATURE:
<223> OTHER INFORMATION: inverted transporter polypeptide

<400> SEQUENCE: 5

Met Tyr Gln Arg Met Leu Arg Cys Gly Ala Glu Leu Gly Ser Pro Gly
  1               5                  10                  15

Gly Gly Ser Ser Gly Gly Ala Gly Gly Arg Leu Ala Leu Leu Trp Ile
             20                  25                  30
```

```
Val Pro Leu Thr Leu Ser Gly Leu Gly Val Ala Trp Gly Ala Ser
         35                  40                  45

Ser Leu Gly Ala His His Ile His His Lys Leu Glu Gln Lys Leu Ile
 50                  55                  60

Ser Glu Glu Asp Leu Gly Gly Leu Ala Asn Pro Thr Arg Val Gly Gly
 65                  70                  75                  80

Arg Glu Pro Tyr Pro Gly Ser Ala Glu Val Ile Arg Glu Ser Ser Ser
                 85                  90                  95

Thr Thr Gly Met Val Val Gly Ile Val Ala Ala Ala Leu Cys Ile
            100                 105                 110

Leu Ile Leu Leu Tyr Ala Met Lys Lys Arg Arg Ala Lys Gly Gly Ser
            115                 120                 125

Gly Gly Ser Gly Gly Leu Glu His Gly Thr Ile Pro Phe Asn Arg Thr
130                 135                 140

His Arg Ser Lys Arg Ser Ser Gly Met Asp Tyr Gly Gly Ala Leu Ser
145                 150                 155                 160

Ala Val Gly Arg Glu Leu Leu Phe Val Thr Asn Pro Val Val Asn
                165                 170                 175

Gly Ser Val Leu Val Pro Glu Asp Gln Cys Tyr Cys Ala Gly Trp Ile
            180                 185                 190

Glu Ser Arg Gly Thr Asn Gly Ala Gln Thr Ala Ser Asn Val Leu Gln
            195                 200                 205

Trp Leu Ala Ala Gly Phe Ser Ile Leu Leu Met Phe Tyr Ala Tyr
210                 215                 220

Gln Thr Trp Lys Ser Thr Cys Gly Trp Glu Glu Ile Tyr Val Cys Ala
225                 230                 235                 240

Ile Glu Met Val Lys Val Ile Leu Glu Phe Phe Phe Glu Phe Lys Asn
                245                 250                 255

Pro Ser Met Leu Tyr Leu Ala Thr Gly His Arg Val Gln Trp Leu Arg
            260                 265                 270

Tyr Ala Thr Trp Leu Leu Thr Cys Pro Val Ile Leu Ile His Leu Ser
            275                 280                 285

Asn Leu Thr Gly Leu Ser Asn Asp Tyr Ser Arg Arg Thr Met Gly Leu
290                 295                 300

Leu Val Ser Asp Ile Gly Cys Ile Val Trp Gly Ala Thr Ser Ala Met
305                 310                 315                 320

Ala Thr Gly Tyr Val Lys Val Ile Phe Phe Cys Leu Gly Leu Cys Tyr
                325                 330                 335

Gly Ala Asn Thr Phe Phe His Ala Ala Lys Ala Tyr Ile Glu Gly Tyr
            340                 345                 350

His Thr Val Pro Lys Gly Arg Cys Arg Gln Val Val Thr Gly Met Ala
            355                 360                 365

Trp Leu Phe Phe Val Ser Trp Gly Met Phe Pro Ile Leu Phe Ile Leu
370                 375                 380

Gly Pro Glu Gly Phe Gly Val Leu Ser Val Tyr Gly Ser Thr Val Gly
385                 390                 395                 400

His Thr Ile Ile Asp Leu Met Ser Lys Asn Cys Trp Gly Leu Leu Gly
                405                 410                 415

His Tyr Leu Arg Val Leu Ile His Glu His Ile Leu Ile His Gly Asp
            420                 425                 430

Ile Arg Lys Thr Thr Lys Leu Asn Ile Gly Gly Thr Glu Ile Glu Val
            435                 440                 445

Glu Thr Leu Val Glu Asp Glu Ala Glu Ala Gly Ala Val Pro Gly Gly
```

```
                    450                 455                 460

Ser Gly Gly Thr Gly Val Ser Lys Gly Glu Glu Leu Phe Thr Gly Val
465                 470                 475                 480

Val Pro Ile Leu Val Glu Leu Asp Gly Asp Val Asn Gly His Lys Phe
                485                 490                 495

Ser Val Ser Gly Glu Gly Glu Gly Asp Ala Thr Tyr Gly Lys Leu Thr
            500                 505                 510

Leu Lys Leu Ile Cys Thr Thr Gly Lys Leu Pro Val Pro Trp Pro Thr
        515                 520                 525

Leu Val Thr Thr Leu Gly Tyr Gly Leu Gln Cys Phe Ala Arg Tyr Pro
    530                 535                 540

Asp His Met Lys Gln His Asp Phe Phe Lys Ser Ala Met Pro Glu Gly
545                 550                 555                 560

Tyr Val Gln Glu Arg Thr Ile Phe Phe Lys Asp Gly Asn Tyr Lys
                565                 570                 575

Thr Arg Ala Glu Val Lys Phe Glu Gly Asp Thr Leu Val Asn Arg Ile
            580                 585                 590

Glu Leu Lys Gly Ile Asp Phe Lys Glu Asp Gly Asn Ile Leu Gly His
        595                 600                 605

Lys Leu Glu Tyr Asn Tyr Asn Ser His Asn Val Tyr Ile Thr Ala Asp
    610                 615                 620

Lys Gln Lys Asn Gly Ile Lys Ala Asn Phe Lys Ile Arg His Asn Ile
625                 630                 635                 640

Glu Asp Gly Gly Val Gln Leu Ala Asp His Tyr Gln Gln Asn Thr Pro
                645                 650                 655

Ile Gly Asp Gly Pro Val Leu Leu Pro Asp Asn His Tyr Leu Ser Tyr
            660                 665                 670

Gln Ser Lys Leu Ser Lys Asp Pro Asn Glu Lys Arg Asp His Met Val
        675                 680                 685

Leu Leu Glu Phe Val Thr Ala Ala Gly Ile Thr Leu Gly Met Asp Glu
    690                 695                 700

Leu Tyr Lys
705

<210> SEQ ID NO 6
<211> LENGTH: 948
<212> TYPE: PRT
<213> ORGANISM: artificial
<220> FEATURE:
<223> OTHER INFORMATION: inverted transporter polypeptide

<400> SEQUENCE: 6

Met Ser Ala Thr Ala Ala Thr Val Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
```

```
                100             105             110
Tyr Phe Ser Thr Gly Gly Ser Gly Gly Ser Arg Gly Val Gln Val Glu
            115             120             125
Thr Ile Ser Pro Gly Asp Gly Arg Thr Phe Pro Lys Arg Gly Gln Thr
            130             135             140
Cys Val Val His Tyr Thr Gly Met Leu Glu Asp Gly Lys Lys Val Asp
145             150             155             160
Ser Ser Arg Asp Arg Asn Lys Pro Phe Lys Phe Met Leu Gly Lys Gln
                165             170             175
Glu Val Ile Arg Gly Trp Glu Glu Gly Val Ala Gln Met Ser Val Gly
                180             185             190
Gln Arg Ala Lys Leu Thr Ile Ser Pro Asp Tyr Ala Tyr Gly Ala Thr
                195             200             205
Gly His Pro Gly Ile Ile Pro Pro His Ala Thr Leu Val Phe Asp Val
            210             215             220
Glu Leu Leu Lys Leu Glu Thr Arg Gly Val Gln Val Glu Thr Ile Ser
225             230             235             240
Pro Gly Asp Gly Arg Thr Phe Pro Lys Arg Gly Gln Thr Cys Val Val
                245             250             255
His Tyr Thr Gly Met Leu Glu Asp Gly Lys Lys Val Asp Ser Ser Arg
            260             265             270
Asp Arg Asn Lys Pro Phe Lys Phe Met Leu Gly Lys Gln Glu Val Ile
            275             280             285
Arg Gly Trp Glu Glu Gly Val Ala Gln Met Ser Val Gly Gln Arg Ala
            290             295             300
Lys Leu Thr Ile Ser Pro Asp Tyr Ala Tyr Gly Ala Thr Gly His Pro
305             310             315             320
Gly Ile Ile Pro Pro His Ala Thr Leu Val Phe Asp Val Glu Leu Leu
            325             330             335
Lys Leu Glu Ser Ala Glu Gln Lys Ile Ser Glu Glu Asp Lys Glu Gln
            340             345             350
Lys Ile Ser Glu Glu Asp Lys Gly Thr Ser Ala Arg Asn Arg Gln Lys
            355             360             365
Arg Ala Ser Gly Thr Glu Gly Arg Gly Ser Leu Leu Thr Cys Gly Asp
            370             375             380
Val Glu Glu Asn Pro Gly Pro Ser Gly Met Asp Tyr Gly Gly Ala Leu
385             390             395             400
Ser Ala Val Gly Arg Glu Leu Leu Phe Val Thr Asn Pro Val Val Val
                405             410             415
Asn Gly Ser Val Leu Val Pro Glu Asp Gln Cys Tyr Cys Ala Gly Trp
            420             425             430
Ile Glu Ser Arg Gly Thr Asn Gly Ala Gln Thr Ala Ser Asn Val Leu
            435             440             445
Gln Trp Leu Ala Ala Gly Phe Ser Ile Leu Leu Met Phe Tyr Ala
            450             455             460
Tyr Gln Thr Trp Lys Ser Thr Cys Gly Trp Glu Glu Ile Tyr Val Cys
465             470             475             480
Ala Ile Glu Met Val Lys Val Ile Leu Glu Phe Phe Glu Phe Lys
            485             490             495
Asn Pro Ser Met Leu Tyr Leu Ala Thr Gly His Arg Val Gln Trp Leu
            500             505             510
Arg Tyr Ala Thr Trp Leu Leu Thr Cys Pro Val Ile Leu Ile His Leu
            515             520             525
```

```
Ser Asn Leu Thr Gly Leu Ser Asn Asp Tyr Ser Arg Arg Thr Met Gly
    530                 535                 540

Leu Leu Val Ser Asp Ile Gly Cys Ile Val Trp Ala Thr Ser Ala
545                 550                 555                 560

Met Ala Thr Gly Tyr Val Lys Val Ile Phe Phe Cys Leu Gly Leu Cys
                565                 570                 575

Tyr Gly Ala Asn Thr Phe Phe His Ala Ala Lys Ala Tyr Ile Glu Gly
            580                 585                 590

Tyr His Thr Val Pro Lys Gly Arg Cys Arg Gln Val Val Thr Gly Met
        595                 600                 605

Ala Trp Leu Phe Phe Val Ser Trp Gly Met Phe Pro Ile Leu Phe Ile
    610                 615                 620

Leu Gly Pro Glu Gly Phe Gly Val Leu Ser Val Tyr Gly Ser Thr Val
625                 630                 635                 640

Gly His Thr Ile Ile Asp Leu Met Ser Lys Asn Cys Trp Gly Leu Leu
                645                 650                 655

Gly His Tyr Leu Arg Val Leu Ile His Glu His Ile Leu Ile His Gly
            660                 665                 670

Asp Ile Arg Lys Thr Thr Lys Leu Asn Ile Gly Gly Thr Glu Ile Glu
        675                 680                 685

Val Glu Thr Leu Val Glu Asp Glu Ala Glu Ala Gly Ala Val Pro Gly
    690                 695                 700

Gly Ser Gly Gly Thr Gly Val Ser Lys Gly Glu Glu Leu Phe Thr Gly
705                 710                 715                 720

Val Val Pro Ile Leu Val Glu Leu Asp Gly Asp Val Asn Gly His Lys
                725                 730                 735

Phe Ser Val Ser Gly Glu Gly Glu Gly Asp Ala Thr Tyr Gly Lys Leu
            740                 745                 750

Thr Leu Lys Leu Ile Cys Thr Thr Gly Lys Leu Pro Val Pro Trp Pro
        755                 760                 765

Thr Leu Val Thr Thr Leu Gly Tyr Gly Leu Gln Cys Phe Ala Arg Tyr
    770                 775                 780

Pro Asp His Met Lys Gln His Asp Phe Phe Lys Ser Ala Met Pro Glu
785                 790                 795                 800

Gly Tyr Val Gln Glu Arg Thr Ile Phe Phe Lys Asp Asp Gly Asn Tyr
                805                 810                 815

Lys Thr Arg Ala Glu Val Lys Phe Glu Gly Asp Thr Leu Val Asn Arg
            820                 825                 830

Ile Glu Leu Lys Gly Ile Asp Phe Lys Glu Asp Gly Asn Ile Leu Gly
        835                 840                 845

His Lys Leu Glu Tyr Asn Tyr Asn Ser His Asn Val Tyr Ile Thr Ala
    850                 855                 860

Asp Lys Gln Lys Asn Gly Ile Lys Ala Asn Phe Lys Ile Arg His Asn
865                 870                 875                 880

Ile Glu Asp Gly Gly Val Gln Leu Ala Asp His Tyr Gln Gln Asn Thr
                885                 890                 895

Pro Ile Gly Asp Gly Pro Val Leu Leu Pro Asp Asn His Tyr Leu Ser
            900                 905                 910

Tyr Gln Ser Lys Leu Ser Lys Asp Pro Asn Glu Lys Arg Asp His Met
        915                 920                 925

Val Leu Leu Glu Phe Val Thr Ala Ala Gly Ile Thr Leu Gly Met Asp
    930                 935                 940
```

Glu Leu Tyr Lys
945

<210> SEQ ID NO 7
<211> LENGTH: 774
<212> TYPE: PRT
<213> ORGANISM: artificial
<220> FEATURE:
<223> OTHER INFORMATION: inverted transporter polypeptide

<400> SEQUENCE: 7

Met Tyr Gln Arg Met Leu Arg Cys Gly Ala Glu Leu Gly Ser Pro Gly
1               5                   10                  15

Gly Gly Ser Ser Gly Gly Ala Gly Gly Arg Leu Ala Leu Leu Trp Ile
            20                  25                  30

Val Pro Leu Thr Leu Ser Gly Leu Leu Gly Val Ala Trp Gly Ala Ser
        35                  40                  45

Ser Leu Gly Ala His His Ile His His Lys Leu Glu Gln Lys Leu Ile
    50                  55                  60

Ser Glu Glu Asp Leu Gly Gly Leu Ala Asn Pro Thr Arg Val Gly Gly
65                  70                  75                  80

Arg Glu Pro Tyr Pro Gly Ser Ala Glu Val Ile Arg Glu Ser Ser Ser
                85                  90                  95

Thr Thr Gly Met Val Val Gly Ile Val Ala Ala Ala Leu Cys Ile
            100                 105                 110

Leu Ile Leu Leu Tyr Ala Met Lys Lys Arg Arg Ala Lys Gly Gly Ser
        115                 120                 125

Gly Gly Ser Gly Gly Leu Glu His Gly Thr Ile Pro Phe Asn Arg Thr
    130                 135                 140

His Arg Ser Lys Arg Ser Ser Gly Met Ser Arg Leu Val Ala Ala Ser
145                 150                 155                 160

Trp Leu Leu Ala Leu Leu Cys Gly Ile Thr Ser Thr Thr Ala
                165                 170                 175

Ser Ser Ala Pro Ala Ala Ser Ser Thr Asp Gly Thr Ala Ala Ala Ala
            180                 185                 190

Val Ser His Tyr Ala Met Asn Gly Phe Asp Glu Leu Ala Lys Gly Ala
        195                 200                 205

Val Val Pro Glu Asp His Phe Val Cys Gly Pro Ala Asp Lys Cys Tyr
    210                 215                 220

Cys Ser Ala Trp Leu His Ser Arg Gly Thr Pro Gly Glu Lys Ile Gly
225                 230                 235                 240

Ala Gln Val Cys Gln Trp Ile Ala Phe Ser Ile Ala Ile Ala Leu Leu
                245                 250                 255

Thr Phe Tyr Gly Phe Ser Ala Trp Lys Ala Thr Cys Gly Trp Glu Glu
            260                 265                 270

Val Tyr Val Cys Cys Val Glu Val Leu Phe Val Thr Leu Glu Ile Phe
        275                 280                 285

Lys Glu Phe Ser Ser Pro Ala Thr Val Tyr Leu Ser Thr Gly Asn His
    290                 295                 300

Ala Tyr Cys Leu Arg Tyr Phe Glu Trp Leu Leu Ser Cys Pro Val Ile
305                 310                 315                 320

Leu Ile Lys Leu Ser Asn Leu Ser Gly Leu Lys Asn Asp Tyr Ser Lys
                325                 330                 335

Arg Thr Met Gly Leu Ile Val Ser Cys Val Gly Met Ile Val Phe Gly
            340                 345                 350

```
Met Ala Ala Gly Leu Ala Thr Asp Trp Leu Lys Trp Leu Leu Tyr Ile
            355                 360                 365
Val Ser Cys Ile Tyr Gly Gly Tyr Met Tyr Phe Gln Ala Ala Lys Cys
        370                 375                 380
Tyr Val Glu Ala Asn His Ser Val Pro Lys Gly His Cys Arg Met Val
385                 390                 395                 400
Val Lys Leu Met Ala Tyr Ala Tyr Phe Ala Ser Trp Gly Ser Tyr Pro
                405                 410                 415
Ile Leu Trp Ala Val Gly Pro Glu Gly Leu Leu Lys Leu Ser Pro Tyr
            420                 425                 430
Ala Asn Ser Ile Gly His Ser Ile Cys Asp Ile Ala Lys Glu Phe
        435                 440                 445
Trp Thr Phe Leu Ala His His Leu Arg Ile Lys Ile His Glu His Ile
        450                 455                 460
Leu Ile His Gly Asp Ile Arg Lys Thr Thr Lys Met Glu Ile Gly Gly
465                 470                 475                 480
Glu Glu Val Glu Val Glu Glu Phe Val Glu Glu Asp Glu Asp Thr
                485                 490                 495
Val Gly Gly Ser Gly Gly Ser Lys Ser Arg Ile Thr Ser Glu Gly Glu
                500                 505                 510
Tyr Ile Pro Leu Asp Gln Ile Asp Ile Asn Gly Gly Ser Gly Gly Thr
            515                 520                 525
Gly Val Ser Lys Gly Glu Glu Leu Phe Thr Gly Val Val Pro Ile Leu
        530                 535                 540
Val Glu Leu Asp Gly Asp Val Asn Gly His Lys Phe Ser Val Ser Gly
545                 550                 555                 560
Glu Gly Glu Gly Asp Ala Thr Tyr Gly Lys Leu Thr Leu Lys Phe Ile
                565                 570                 575
Cys Thr Thr Gly Lys Leu Pro Val Pro Trp Pro Thr Leu Val Thr Thr
            580                 585                 590
Leu Thr Tyr Gly Val Gln Cys Phe Ser Arg Tyr Pro Asp His Met Lys
        595                 600                 605
Gln His Asp Phe Phe Lys Ser Ala Met Pro Glu Gly Tyr Val Gln Glu
        610                 615                 620
Arg Thr Ile Phe Phe Lys Asp Asp Gly Asn Tyr Lys Thr Arg Ala Glu
625                 630                 635                 640
Val Lys Phe Glu Gly Asp Thr Leu Val Asn Arg Ile Glu Leu Lys Gly
                645                 650                 655
Ile Asp Phe Lys Glu Asp Gly Asn Ile Leu Gly His Lys Leu Glu Tyr
            660                 665                 670
Asn Tyr Asn Ser His Asn Val Tyr Ile Met Ala Asp Lys Gln Lys Asn
        675                 680                 685
Gly Ile Lys Val Asn Phe Lys Ile Arg His Asn Ile Glu Asp Gly Ser
        690                 695                 700
Val Gln Leu Ala Asp His Tyr Gln Gln Asn Thr Pro Ile Gly Asp Gly
705                 710                 715                 720
Pro Val Leu Leu Pro Asp Asn His Tyr Leu Ser Thr Gln Ser Lys Leu
                725                 730                 735
Ser Lys Asp Pro Asn Glu Lys Arg Asp His Met Val Leu Leu Glu Phe
            740                 745                 750
```

```
Val Thr Ala Ala Gly Ile Thr Leu Gly Met Asp Glu Leu Tyr Lys Phe
            755                 760                 765
Cys Tyr Glu Asn Glu Val
    770
```

INVERTED TRANSPORTER POLYPEPTIDES AND METHODS OF USING

CROSS-REFERENCE TO RELATED APPLICATIONS

This application is a national stage application under 35 U.S.C. § 371 of PCT International Application No. PCT/US2019/035344, filed on Jun. 4, 2019, which claims the benefit of U.S. Patent Application Ser. No. 62/680,130, filed on Jun. 4, 2018. The disclosure of the prior applications are considered part of (and are incorporated by reference in) the disclosure of this application.

BACKGROUND

1. Technical Field

This document relates to methods and materials for modulating one or more properties of transporter proteins. For example, this document provides inverted transporter polypeptides including a leader sequence fused to a transporter protein. In some cases, one or more inverted transporter polypeptides can be used to alter (e.g., stimulate or inhibit) the excitability of one or more cells (e.g., neurons and myocytes).

2. Background Information

Transporters are distinguished by intramolecular ion coordination and conformational changes that restrict and permit, in sequence, access to internal and external compartments. Rhodopsin family members that appear to behave like transporters have properties of both transporters and channels, reflecting a proposed functional continuum (Gadsby, 2009 Nature reviews Molecular cell biology 10:344-352): their currents show strong dependence on electrochemical gradients, but the flux is markedly lower than that of channels.

SUMMARY

This document provides methods and materials for modulating one or more properties of transporter proteins. For example, this document provides inverted transporter proteins including a leader sequence fused to a transporter protein. For example, this document also provides methods for altering (e.g., stimulating or inhibiting) the excitability of one or more cells (e.g., neurons and myocytes). In some cases, one or more inverted transporter proteins (e.g., in the plasma membrane of a cell) can be used to inhibit excitability of one or more neurons and/or to inhibit excitability of one or more myocytes.

As demonstrated herein, a light-gated inhibitor of neural activity, FLInChR, was generated by topological inversion of a Channelrhodopsin (ChR). FLInChR (Full Length Inversion of ChR)—a fusion between the transmembrane domain of Neurexin 1B and a E123T/T159C variant of ChR 2-displays efficient membrane targeting and responds to light with robust outward current. In brain slices, FLInChR sustained suppression of action potential generation for prolonged periods, and displayed enough precision for the "deletion" of individual action potentials in high frequency trains. Also demonstrated herein, topological inversion CsChrimson, a cation channel displayed markedly greater selectivity for K+ over Na+.

Having the ability to modify membrane topology (e.g., by topological inversion of transporter proteins) provides a unique and unrealized opportunity to enable targeted manipulation of activity in specific populations of cells (e.g., neurons). Targeted manipulation can be used to alter (e.g., stimulate or inhibit) the excitability of one or more cells (e.g., neurons and myocytes) to treat a mammal having a disease or disorder characterized by altered cellular excitability. Targeted manipulation also can be used in neuroscience research to investigate the neural basis of behavior by, for example, using membrane topology to evaluate, for example, structure-function studies of permeation in transporter proteins.

In general, one aspect of this document features inverted transporter polypeptides. An inverted transporter polypeptide can include a leader sequence and a transporter protein. The transporter protein can include an extracellular N-terminus and can present the extracellular N-terminus on the intracellular side of a cell membrane. The inverted transporter polypeptide can inhibit the excitability of one or more cells. The one or more cells can include one or more neurons. The one or more cells can include one or more myocytes. The leader sequence can include a transmembrane domain of an integral membrane protein. The integral membrane protein can be Neurexin 1B, synaptobrevin, or a Drosophila olfactory receptor. The transporter protein can include a light-gated ion channel. The transporter protein can include a light-sensitive receptor protein. The light-sensitive receptor protein can be a rhodopsin. The rhodopsin can be a channelrhodopsin, an archaerhodopsin, or a halorhodopsin. An inverted transporter polypeptide can have a leader sequence including a transmembrane domain of Neurexin 1B and a transporter protein including a channelrhodopsin. An inverted transporter polypeptide can have a leader sequence including a transmembrane domain of synpatobrevin and a transporter protein including a channelrhodopsin. The channelrhodopsin can include a substitution of the glutamic acid at residue 123 with a threonine (E123T). The channelrhodopsin can include a substitution of the threonine at residue 159 with a cysteine (T159C). The channelrhodopsin can include both a E123T substitution and a T159C substitution. The inverted transporter polypeptide can include the sequence set forth in SEQ ID NO:5. The inverted transporter polypeptide can include the sequence set forth in SEQ ID NO:6. The inverted transporter polypeptide can include the sequence set forth in SEQ ID NO:7.

In another aspect, this document features a nucleic acid encoding any one of the inverted transporter polypeptides described herein. A nucleic acid encoding an inverted transporter polypeptide can include a nucleic acid encoding a leader sequence. The nucleic acid can be a viral vector (e.g., an adenoviral vector).

In another aspect, this document features a method for inverting a transporter protein in a cell. The methods can include, or consist essentially of, expressing a nucleic acid encoding a leader sequence conjugated to a nucleic acid encoding a transporter protein in a cell such that the nucleic acid expresses an inverted transporter polypeptide. The nucleic acid can be a viral vector (e.g., an adenoviral vector).

In another aspect, this document features a method for altering the excitability of a cell. The methods can include, or consist essentially of, administering nucleic acid encoding a leader sequence conjugated to a nucleic acid encoding a transporter protein to a cell, such that the nucleic acid expresses an inverted transporter polypeptide where the inverted transporter polypeptide can regulate the excitability of the cell. The nucleic acid can be a viral vector (e.g., an adenoviral vector). The altering can include inhibiting the excitability of a cell. The cell can be a neuron. The cell can be a myocyte. The regulation can be photoinhibition.

In another aspect, this document features a method for treating a mammal having a disease or disorder characterized by altered cellular excitability. The methods can include, or consist essentially of, administering an inverted transporter polypeptide to a mammal. The mammal can be a human. The administering can include administering a nucleic acid encoding a leader sequence conjugated a nucleic acid encoding a transporter protein, where the nucleic acid expresses an inverted transporter polypeptide. The nucleic acid can be a viral vector (e.g., an adenoviral vector). The altering can include inhibiting the excitability of a cell. The cell can be a neuron. The cell can be a myocyte. The regulation can be photoinhibition.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 4. Opsin inversion generates novel functionality. A, Action spectrum of native and inverted CsChrimson in hippocampal neuronal cultures. B, Current-voltage relationship for native (n=5) and inverted (n=5) CsChrimson. Note a shift of the reversal potential towards the reversal potential for potassium. C, Current amplitude as a function of holding potential in three different internal solutions for inverted Channelrhodopsin 2 ET/TC. Note the lack of current reversal. D, Action spectrum for native (n=4) and inverted (n=4) Channelrhodopsin 2 ET/TC and FLInChR. E, Amplitude of light-evoked current amplitude in physiological conditions and following wholesale replacement of external ions by sucrose. F, Current amplitude during bidirectional manipulation of internal pH (n=5, see Methods). E, Amplitude of light-evoked current following ion substitutions. Error bars represent standard error of the mean. *, p<0.05, one-way ANOVA with post-hoc Tukey's test. All currents were characterized in response to 2 ms light pulses (widefield illumination, 10 mW/mm2 at the focal plane of the objective).

Distribution of latencies for light-dependent suppression of spiking across neurons. J. Repeated photoinhibition in an example juxta-cellular recording from a mouse layer 5 projection neuron. Note efficient suppression of spiking throughout the duration of illumination. K, Activity in three example mouse projection neurons for 60 repeated light presentations. L, Distribution of light-dependent modulation effects across cortical layers. Notice that robust short-latency inhibition is confined to layer 5.

Figure 10A:
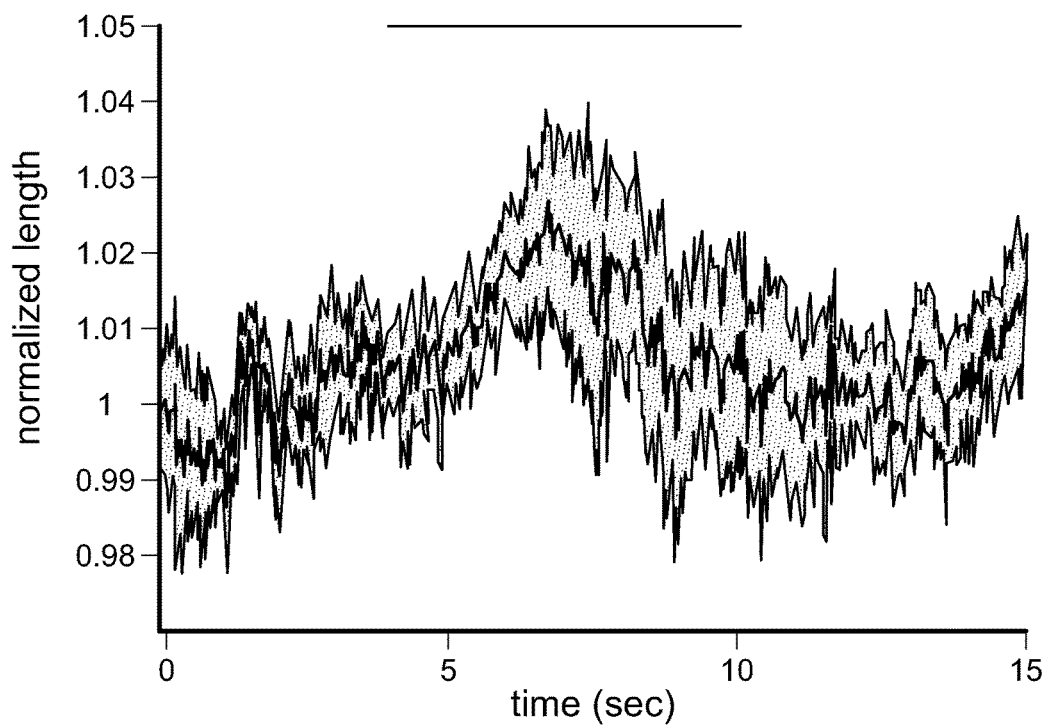
Figure 10B:
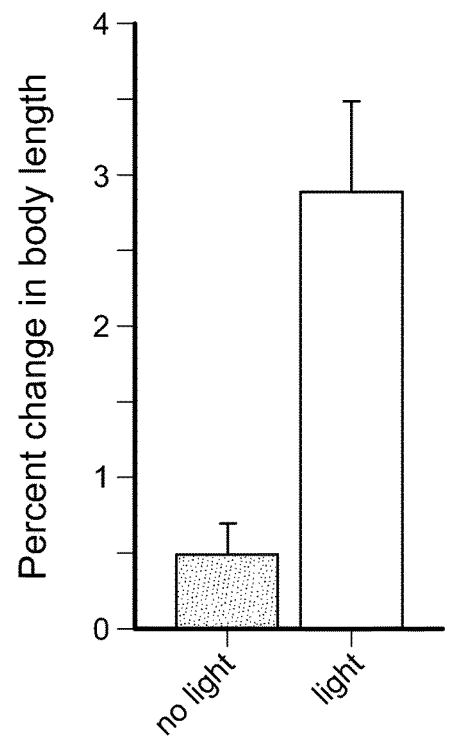

FIG. 10. FLInChR-mediated hyperpolarization of body wall muscles induces body elongations in ('. elegans. Mean normalized body length (+SEM) relative to the initial length in animals expressing FLInChR in body-wall muscles. Left panel: time course of muscle elongation. Right panel: average percent change in body length over a 5 second window before and after onset of illumination.

DETAILED DESCRIPTION

This document relates to methods and materials for modulating one or more properties of one or more transporter proteins. For example, this document provides inverted transporter polypeptides, nucleic acids encoding inverted transporter polypeptides, and methods for inverting transporter polypeptides (e.g., in the plasma membrane of a cell). In some cases, inverted transporter polypeptides can include a leader sequence fused to a transporter protein (e.g., a transporter protein having an extracellular N-terminus). As used herein, an "inverted" transporter polypeptide is any transporter polypeptide where fusion to a leader sequence described herein results in the inversion of the full-length transporter protein or a portion (e.g., a terminus, a helix, or a loop) of the transporter protein within the plasma membrane of a cell. For example, inverted transporter polypeptides provided herein can include a leader sequence and a transporter protein having an extracellular N-terminus (e.g., in the non-inverted (e.g., endogenous) conformation of the transporter protein), and can be an inverted such that the extracellular N-terminus of the transporter protein is presented on the intracellular side of a cell membrane. As described herein, inverted transporter polypeptides provided herein can have one or more properties of the transporter protein modulated (e.g., enhanced, inhibited, shifted, or reversed) relative to a transporter protein that is not inverted. Also provided herein are methods of using inverted transporter polypeptides provided herein. For example, one or more inverted transporter polypeptides provided herein can be used to alter (e.g., stimulate or inhibit) the excitability of one or more cells (e.g., neurons and myocytes). In some cases, the excitability of one or more cells can be altered by modulating (e.g., enhancing, inhibiting, shifting, or reversing) one or more properties of the transporter protein (e.g., relative to a transporter protein that is not inverted). For example, one or more inverted transporter polypeptides can be used to inhibit excitability of one or more neurons (e.g., one or more neurons within a mammal). In some cases, the excitability of one or more cells can be altered by modulating (e.g., enhancing, inhibiting, shifting, or reversing) one or more properties of the transporter protein (e.g., relative to a transporter protein that is not inverted) as described herein.

Inverted transporter polypeptides described herein (e.g., containing a leader sequence and a transporter protein) can include any appropriate transporter protein. A transporter protein can be synthetic (e.g., recombinant) or naturally occurring. A transporter protein can be a full-length transporter protein or a fragment of a transporter protein. In some cases, a transporter protein can be a gated-transporter protein (e.g., a light-gated transporter protein such as a light-gated ion channel, a voltage-gated transporter protein such as a voltage-gated ion channel (VIC), and a ligand-gated transporter protein such as a ligand-gated ion channels (LGICs)). In some cases, a transporter protein can be a light-sensitive protein. In some cases, a transporter protein can be a receptor protein. In some cases, a transporter protein can be both a light-sensitive protein and a receptor protein. For example, a transporter protein can be a light-sensitive receptor protein (e.g., a light-sensitive receptor protein involved in visual phototransduction). In some cases, a transporter protein can be a seven-transmembrane protein. In some cases, a transporter protein can be a pump. In some cases, a transporter protein can be a channel. In some cases, a transporter protein can be both a pump and a channel. In some cases, a transporter protein can be a G-protein-coupled receptor (GPCR) protein. In some cases, a transporter protein can be a pigment (e.g., a biological pigment) protein. In some cases, a transporter protein can have an extracellular N-terminus. Examples of transporter proteins that can be included in an inverted transporter polypeptide described herein can include, without limitation, rhodopsins (e.g., channelrhodopsins (ChR) such as ChR1 and ChR2, archaerhodopsin (ArchT), halorhodopsin, Chrimson, and Chronos).

In some cases, an inverted transporter polypeptide described herein can include a ChR protein. Exemplary ChR polypeptides (and nucleotides encoding exemplary ChR polypeptides) can be as set forth in the National Center for Biotechnology Information (NCBI) sequence databases at, for example, Accession No. 6EID_A, and Accession No. 6EID_B. A representative ChR polypeptide sequence is as follows.

```
                                           SEQ ID NO: 1
MDYGGALSAVGRELLFVTNPVVVNGSVLVPEDQCYCAGWIESRGTNGAQ

TASNVLQWLAAGFSILLLMFYAYQTWKSTCGWEEIYVCAIEMVKVILEF

FFEFKNPSMLYLATGHRVQWLRYAEWLLTCPVILIHLSNLTGLSNDYSR

RTMGLLVSDIGTIVWGATSAMATGYVKVIFFCLGLCYGANTFFHAAKAY

IEGYHTVPKGRCRQVVTGMAWLFFVSWGMFPILFILGPEGFGVLSVYGS

TVGHTIIDLMSKNCWGLLGHYLRVLIHEHILIHGDIRKTTKLNIGGTEI

EVETLVEDEAEAGAV
```

In some cases, an inverted transporter polypeptide described herein can include a Chrimson protein. Exemplary Chrimson polypeptides (and nucleotides encoding exemplary Chrimson polypeptides) can be as set forth in the NCBI sequence databases at, for example, Accession No. AHH02126.1 (e.g., Version AHH02126.1), and Accession No. AIE89247 (e.g., Version AIE89247.2). A representative Chrimson polypeptide sequence is as follows

```
                                           SEQ ID NO: 2
MSRLVAASWLLALLLCGITSTTTASSAPAASSTDGTAAAAVSHYAMNGF

DELAKGAVVPEDHFVCGPADKCYCSAWLHSRGTPGEKIGAQVCQWIAFS

IAIALLTFYGFSAWKATCGWEEVYVCCVEVLFVTLEIFKEFSSPATVYL

STGNHAYCLRYFEWLLSCPVILIKLSNLSGLKNDYSKRTMGLIVSCVGM

IVFGMAAGLATDWLKWLLYIVSCIYGGYMYFQAAKCYVEANHSVPKGHC

RMVVKLMAYAYFASWGSYPILWAVGPEGLLKLSPYANSIGHSICDIIAK

EFWTFLAHHLRIKIHEHILIHGDIRKTTKMEIGGEEVEVEEFVEEEDED

TV
```

In some cases, an inverted transporter polypeptide described herein can include a variant of a transporter protein described herein. The term "variant" as used herein refers to an amino acid sequence that is at least 85 percent (e.g., at least 85, 90, 95, 99, or 100 percent) identical to the wild type sequence, provided that the variant maintains the features (e.g., the function and any secondary, tertiary, and/or quaternary structure(s)) of the wild type protein. In some cases, a variant polypeptide can have at least 6 (e.g., 6, 7, 8, 9, 10, 11, 12, 13, 14, 15, 16, 17, 18, 19, 20, 21, 22, 23, 24, 25, or more) amino acid residues modified (e.g., substituted) relative to the wild type sequence, provided that the variant maintains the features (e.g., the function and any secondary, tertiary, and/or quaternary structure(s)) of the wild type protein. For example, a variant ChR2 polypeptide can include any sequence that is at least 85 percent (e.g., at least 85, 90, 95, 99, or 100 percent) identical to the sequence set forth in SEQ ID NO:1. In some cases, a variant ChR2 polypeptide can include a substitution of the glutamic acid (E) at residue 123 (e.g., residue 123 as shown in SEQ ID NO:1) with a threonine (T) (e.g., a E123T substitution). In some cases, a variant ChR2 polypeptide can include a substitution of the T at residue 159 (e.g., residue 159 as shown in SEQ ID NO:1) with a cysteine (C) (e.g., a T159C substitution). In some cases, a variant ChR2 polypeptide can include both a E123T substitution and a T159C substitution.

Inverted transporter polypeptides described herein (e.g., containing a leader sequence and a transporter protein) can include a transporter protein obtained from any appropriate source. In some cases, a transporter protein can be a microbial transporter protein. In some cases, a transporter protein can be a mammalian transporter protein. Examples of sources from which transporter proteins can be obtained include, without limitation, green algae (e.g., chlamydomonas), fungi, plants, and metazoan. For example, a transporter protein (e.g., ChR2) can be obtained from chlamydomonas (e.g., Chlamydomonas reinhardtii).

Inverted transporter polypeptides described herein (e.g., containing a leader sequence and a transporter protein) can include any appropriate leader sequence. In some cases, a leader sequence can be a polypeptide sequence. In some cases, a leader sequence can include a transmembrane domain. In some cases, a leader sequence can include a signal sequence. In some cases, a leader sequence can be obtained from an integral membrane protein (e.g., a type-I integral membrane protein). Examples of leader sequences that can be included in an inverted transporter polypeptide described herein include, without limitation, a Neurexin 1B transmembrane domain, a synaptobrevin transmembrane domain, and a *Drosophila* olfactory receptor transmembrane domain. Examples of leader sequences include, without limitation, the following amino acid sequences.

```
                                           SEQ ID NO: 3
MYQRMLRCGAELGSPGGGSSGGAGGRLALLWIVPLTLSGLLGVAWGASS

LGAHHIHHKLEQKLISEEDLGGLANPTRVGGREPYPGSAEVIRESSSTT

GMVVGIVAAAALCILILLYAMKKRRAKGGSGGSGGLEHGTIPFNRTHRS

KRSSG

SEQ ID NO: 4
MSATAATVPPAAPAGEGGPPAPPPNLTSNRRLQQTQAQVDEVVDIMRVN

VDKVLERDQKLSELDDRADALQAGASQFETSAAKLKRKYWWKNLKMMII

LGVICAIILIIIIVYFSTGGSGGSRGVQVETISPGDGRTFPKRGQTCVV

HYTGMLEDGKKVDSSRDRNKPFKFMLGKQEVIRGWEEGVAQMSVGQRAK

LTISPDYAYGATGHPGIIPPHATLVFDVELLKLETRGVQVETISPGDGR

TFPKRGQTCVVHYTGMLEDGKKVDSSRDRNKPFKFMLGKQEVIRGWEEG

VAQMSVGQRAKLTISPDYAYGATGHPGIIPPHATLVFDVELLKLESAEQ

KISEEDKEQKISEEDKGTSARNRQKRASGTEGRGSLLTCGDVEENPGPS

G
```

Inverted transporter polypeptides described herein (e.g., containing a leader sequence and a transporter protein) can include a leader sequence obtained from any appropriate source.

In some cases, inverted transporter polypeptides described herein can include a Neurexin 1B transmembrane domain leader sequence and a ChR transporter protein. A representative inverted transporter polypeptide including a Neurexin 1B leader sequence and ChR transporter protein is as follows.

SEQ ID NO: 5
MYQRMLRCGAELGSPGGGSSGGAGGRLALLWIVPLTLSGLLGVAWGASS

LGAHHIHHKLEQKLISEEDLGGLANPTRVGGREPYPGSAEVIRESSSTT

GMVVGIVAAAALCILILLYAMKKRRAKGGSGGSGGLEHGTIPFNRTHRS

KRSSGMDYGGALSAVGRELLFVTNPVVVNGSVLVPEDQCYCAGWIESRG

TNGAQTASNVLQWLAAGFSILLLMFYAYQTWKSTCGWEEIYVCAIEMVK

VILEFFFEFKNPSMLYLATGHRVQWLRYATWLLTCPVILIHLSNLTGLS

NDYSRRTMGLLVSDIGCIVWGATSAMATGYVKVIFFCLGLCYGANTFFH

AAKAYIEGYHTVPKGRCRQVVTGMAWLFFVSWGMFPILFILGPEGFGVL

SVYGSTVGHTIIDLMSKNCWGLLGHYLRVLIHEHILIHGDIRKTTKLNI

GGTEIEVETLVEDEAEAGAVPGGSGGTGVSKGEELFTGVVPILVELDGD

VNGHKFSVSGEGEGDATYGKLTLKLICTTGKLPVPWPTLVTTLGYGLQC

FARYPDHMKQHDFFKSAMPEGYVQERTIFFKDDGNYKTRAEVKFEGDTL

VNRIELKGIDFKEDGNILGHKLEYNYNSHNVYITADKQKNGIKANFKIR

HNIEDGGVQLADHYQQNTPIGDGPVLLPDNHYLSYQSKLSKDPNEKRDH

MVLLEFVTAAGITLGMDELYK

In some cases, inverted transporter polypeptides described herein can include a synaptobrevin transmembrane domain leader sequence and a ChR transporter protein. A representative inverted transporter polypeptide including a synaptobrevin leader sequence and a ChR transporter protein is as follows.

SEQ ID NO: 6
MSATAATVPPAAPAGEGGPPAPPPNLTSNRRLQQTQAQVDEVVDIMRVN

VDKVLERDQKLSELDDRADALQAGASQFETSAAKLKRKYWWKNLKMMII

LGVICAIILIIIVYFSTGGSGGSRGVQVETISPGDGRTFPKRGQTCVV

HYTGMLEDGKKVDSSRDRNKPFKFMLGKQEVIRGWEEGVAQMSVGQRAK

LTISPDYAYGATGHPGIIPPHATLVEDVELLKLETRGVQVETISPGDGR

TFPKRGQTCVVHYTGMLEDGKKVDSSRDRNKPFKFMLGKQEVIRGWEEG

VAQMSVGQRAKLTISPDYAYGATGHPGIIPPHATLVEDVELLKLESAEQ

KISEEDKEQKISEEDKGTSARNRQKRASGTEGRGSLLTCGDVEENPGPS

GMDYGGALSAVGRELLFVTNPVVVNGSVLVPEDQCYCAGWIESRGTNGA

QTASNVLQWLAAGFSILLLMFYAYQTWKSTCGWEEIYVCAIEMVKVILE

FFFEFKNPSMLYLATGHRVQWLRYATWLLTCPVILIHLSNLTGLSNDYS

RRTMGLLVSDIGCIVWGATSAMATGYVKVIFFCLGLCYGANTFFHAAKA

YIEGYHTVPKGRCRQVVTGMAWLFFVSWGMFPILFILGPEGFGVLSVYG

STVGHTIIDLMSKNCWGLLGHYLRVLIHEHILIHGDIRKTTKLNIGGTE

IEVETLVEDEAEAGAVPGGSGGTGVSKGEELFTGVVPILVELDGDVNGH

KFSVSGEGEGDATYGKLTLKLICTTGKLPVPWPTLVTTLGYGLQCFARY

PDHMKQHDFFKSAMPEGYVQERTIFFKDDGNYKTRAEVKFEGDTLVNRI

ELKGIDFKEDGNILGHKLEYNYNSHNVYITADKQKNGIKANFKIRHNIE

DGGVQLADHYQQNTPIGDGPVLLPDNHYLSYQSKLSKDPNEKRDHMVLL

EFVTAAGITLGMDELYK

In some cases, inverted transporter polypeptides described herein can include a Neurexin 1B transmembrane domain leader sequence and a Chrimson transporter protein. A representative inverted transporter polypeptide including a Neurexin 1B leader sequence and Chrimson transporter protein is as follows.

SEQ ID NO: 7
MYQRMLRCGAELGSPGGGSSGGAGGRLALLWIVPLTLSGLLGVAWGASS

LGAHHIHHKLEQKLISEEDLGGLANPTRVGGREPYPGSAEVIRESSSTT

GMVVGIVAAAALCILILLYAMKKRRAKGGSGGSGGLEHGTIPFNRTHRS

KRSSGMSRLVAASWLLALLLCGITSTTTASSAPAASSTDGTAAAAVSHY

AMNGFDELAKGAVVPEDHFVCGPADKCYCSAWLHSRGTPGEKIGAQVCQ

WIAFSIAIALLTFYGFSAWKATCGWEEVYVCCVEVLFVTLEIFKEFSSP

ATVYLSTGNHAYCLRYFEWLLSCPVILIKLSNLSGLKNDYSKRTMGLIV

SCVGMIVFGMAAGLATDWLKWLLYIVSCIYGGYMYFQAAKCYVEANHSV

PKGHCRMVVKLMAYAYFASWGSYPILWAVGPEGLLKLSPYANSIGHSIC

DIIAKEFWTFLAHHLRIKIHEHILIHGDIRKTTKMEIGGEEVEVEEFVE

EEDEDTVGGSGGSKSRITSEGEYIPLDQIDINGGSGGTGVSKGEELFTG

VVPILVELDGDVNGHKFSVSGEGEGDATYGKLTLKFICTTGKLPVPWPT

LVTTLTYGVQCFSRYPDHMKQHDFFKSAMPEGYVQERTIFFKDDGNYKT

RAEVKFEGDTLVNRIELKGIDFKEDGNILGHKLEYNYNSHNVYIMADKQ

KNGIKVNFKIRHNIEDGSVQLADHYQQNTPIGDGPVLLPDNHYLSTQSK

LSKDPNEKRDHMVLLEFVTAAGITLGMDELYKFCYENEV

In some cases, inverted transporter polypeptides described herein also can include one or more additional components. In some cases, an inverted transporter polypeptide also can include a label (e.g., a detectable label). Examples of detectable labels include, without limitation, polypeptide tags (e.g., a myc tag, a histidine tag, and a FLAG tag), and fluorescent tags (e.g., green fluorescent protein (GFP), yellow fluorescent protein (YFP), blue fluorescent protein (BFP), and cyan fluorescent protein (CFP)).

Also provided herein are nucleic acids (e.g., nucleic acid constructs) encoding inverted transporter polypeptides described herein. A nucleic acid encoding an inverted transporter polypeptide described herein can include any appropriate type of nucleic acid. Examples of nucleic acids include, without limitation, DNA, RNA, and hybrids thereof. A nucleic acid can be single stranded, double stranded, or a combination there (e.g., having one or more portions of the nucleic acid that are single stranded and having one or more portions of the nucleic acid that are double stranded).

A nucleic acid construct can be any appropriate construct. In some cases, a nucleic acid construct can be an expression construct. Examples of nucleic acid constructs include, without limitation, plasmids and viral vectors. In some cases, a nucleic acid construct encoding an inverted transporter polypeptide can be a viral vector (e.g., an adeno associated virus (AAV, such as AAV1 or AAV2) vector, a retroviral vector, and a lentiviral vector). For example, a nucleic acid construct encoding an inverted transporter polypeptide can be an AAV vector.

In some cases, nucleic acids (e.g., nucleic acid constructs) encoding inverted transporter polypeptides described herein also can include one or more additional components. In some cases, an inverted transporter polypeptide also can include one or more regulatory elements. Examples of regulatory elements include, without limitation, promoters (e.g., CAG), enhancers, nucleic acids encoding a label (e.g., a detectable label), one or more loxP sites, and one or more FRT sites. For example, a nucleic acid construct encoding an inverted transporter polypeptide also can include a CAG promoter to drive expression of the nucleic acid encoding an inverted transporter polypeptide.

Inverted transporter polypeptides described herein (e.g., containing a leader sequence and a transporter protein) can have one or more modulated (e.g., enhanced, inhibited, shifted, or reversed) properties of the transporter protein (e.g., relative to a transporter protein that is not inverted). The transporter protein property can be any appropriate property of the transporter protein. Examples of properties of transporter proteins include, without limitation, the transporter regulation (e.g., the stimulus/stimuli regulating transport and/or the sensitivity to stimulus/stimuli regulating transport), the transporter function (e.g., the molecule(s) being transported, the selectivity of the molecule(s) being transported, and/or the direction of transport), and the transporter conduction mechanism.

In some cases, inverted transporter polypeptides described herein (e.g., containing a leader sequence and a transporter protein) can modulate (e.g., enhance, inhibit, shift, or reverse) the regulation (e.g., gating) of the transporter (e.g., the stimulus/stimuli regulating transport and/or the sensitivity to stimulus/stimuli regulating transport) relative to a transporter protein that is not inverted. Inverted transporter polypeptides described herein can modulate any appropriate type of transporter gating. Examples of stimuli that can regulate transporter gating include, without limitation, light, electromagnetic radiation, voltage, ligands, and temperature. In some cases, the activity of an inverted transporter polypeptides having modulated regulation can be controlled (e.g., by providing or withholding a stimulus). For example, the activity of an inverted transporter polypeptide (e.g., containing a Neurexin 1B transmembrane domain leader sequence and a ChR transporter protein) can be inhibited in the presence of light (e.g., photoinhibition).

In some cases, inverted transporter polypeptides described herein (e.g., containing a leader sequence and a transporter protein) can modulate (e.g., enhance, inhibit, shift, or reverse) the function of the transporter (e.g., the molecule(s) being transported, the selectivity of the molecule(s) being transported, and/or the direction of transport) relative to a transporter protein that is not inverted. Inverted transporter polypeptides described herein can modulate transport of any appropriate molecule. Examples of molecules that can be transported by a transporter protein include, without limitation, ions (e.g., sodium ($Na^+$), potassium ($K^+$), calcium ($Ca^{2+}$), chloride ($Cl^-$), $HCO^{3-}$(bicorabonate), and tetraethylammonium ($TEA^+$)), gases (e.g., $CO_2$, $N_2$, $O_2$), uncharged polar molecules (e.g., urea, water, ethanol, glucose, and fructose), and charged polar molecules (e.g., ATP, amino acids, and glucose-6-phosphate). In some cases, an inverted transporter polypeptide can have increased ion permeability. An inverted transporter polypeptide can have any appropriate level of increased ion permeability. For example, an inverted transporter polypeptide (e.g., containing a Neurexin 1B transmembrane domain leader sequence and a Chrimson transporter protein) can have increased $K+$ ion permeability (e.g., about 7-8 fold increased $K+$ permeability). For example, an inverted transporter polypeptide (e.g., containing a Neurexin 1B transmembrane domain leader sequence and a Chrimson transporter protein) can have selectivity for $K+$ ions over $Na+$ ions.

Also provided herein are methods of inverting transporter proteins (e.g., containing a leader sequence and a transporter protein). For example, a leader sequence described herein can be conjugated (e.g., fused) to a transporter protein described herein to produce inverted transporter polypeptides described herein. For example, nucleic acid encoding a leader sequence described herein can be conjugated (e.g., fused) to a nucleic acid encoding a transporter protein described herein, and the conjugated nucleic acid can be expressed in a cell to produce inverted transporter polypeptides described herein. In some cases, a transporter protein containing an extracellular N-terminus can be inverted by fusing a Neurexin 1B transmembrane domain leader sequence to the transporter protein. In some cases, a transporter protein containing an extracellular N-terminus can be inverted by fusing a synaptobrevin transmembrane domain leader sequence to the transporter protein. In some cases, a transporter protein containing an extracellular N-terminus can be inverted by fusing a *Drosophila* olfactory receptor transmembrane domain leader sequence to the transporter protein.

In some cases, methods of inverting transporter proteins can produce inverted transporter polypeptides having one or more properties of the transporter protein modulated (e.g., enhanced, inhibited, shifted, or reversed) as described herein (e.g., relative to a transporter protein that is not inverted). For example, a rhodopsin transporter protein (e.g., ChR2) can be inverted as described herein to produce an inverted rhodopsin that can be regulated with light.

Also provided herein are methods of using inverted transporter polypeptides provided herein (e.g., containing a leader sequence and a transporter protein). For example, one or more inverted transporter polypeptides provided herein (e.g., in the plasma membrane of a cell) can be used to alter (e.g., stimulate or inhibit) the excitability of one or more cells (e.g., neurons and myocytes). In some cases, the excitability of one or more cells can be altered by modulating (e.g., enhancing, inhibiting, shifting, or reversing) one or more properties of the transporter protein (e.g., relative to a transporter protein that is not inverted) as described herein. For example, one or more inverted transporter polypeptides can be used to inhibit excitability of one or more neurons (e.g., one or more neurons within a mammal). In cases where an inverted transporter polypeptide includes a gated-transporter protein, the activity of the inverted transporter polypeptide can be controlled (e.g., by providing or withholding the stimulus). For example, the activity of an inverted transporter polypeptide including a gated-transporter protein can be controlled in temporal and/or spatial manner.

Inverted transporter polypeptides provided herein (e.g., containing a leader sequence and a transporter protein) can be used to treat any appropriate disease or disorder characterized by altered cellular excitability. In some cases, a disease or disorder characterized by altered cellular excitability can include altered excitability of one or more neurons. For example, one or more inverted transporter polypeptides can be used to inhibit excitability of one or more neurons in a mammal having a disease or disorder characterized by altered cellular excitability can include altered excitability of one or more neurons to treat the mammal. In some cases, a disease or disorder characterized by altered cellular excitability can include altered excitability of one or more myocytes. For example, one or more inverted transporter polypeptides can be used to inhibit excitability of one or more myocytes in a mammal having a disease or disorder characterized by altered cellular excitability can include altered excitability of one or more myocytes to treat the mammal.

Inverted transporter polypeptides provided herein (e.g., containing a leader sequence and a transporter protein), or nucleic acids encoding one or more inverted transporter polypeptides described herein, can be used to treat any appropriate type of mammal (e.g., a mammal having or at risk for developing a disease or disorder characterized by altered cellular excitability). Examples of mammals that can be treated with one or more inverted transporter polypeptides described herein include, without limitation, humans, non-human primates (e.g., monkeys), dogs, cats, horses, cows, pigs, sheep, rabbits, mice, and rats. For example, humans having or at risk of developing a disease or disorder characterized by altered cellular excitability can be treated with one or more inverted transporter polypeptides or nucleic acids encoding one or more inverted transporter polypeptides as described herein.

In some cases, the methods provided herein can include identifying a mammal as having or at risk for developing a disease or disorder characterized by altered cellular excitability. Any appropriate method can be used to identify a mammal having or at risk for developing a disease or disorder characterized by altered cellular excitability.

A mammal identified as having or at risk for developing a disease or disorder characterized by altered cellular excitability can be administered or instructed to self-administer one or more (e.g., one, two, three, four, five, or more) inverted transporter polypeptides described herein (e.g., containing a leader sequence and a transporter protein). In some cases, a mammal identified as having or at risk for developing a disease or disorder characterized by altered cellular excitability can be administered or instructed to self-administer one or more one or more nucleic acids encoding one or more inverted transporter polypeptides described herein.

Inverted transporter polypeptides described herein (e.g., containing a leader sequence and a transporter protein), or nucleic acid encoding one or more inverted transporter polypeptides described herein, can be used to alter the excitability of any type of cell in a mammal. Examples of excitable cells include, without limitation, neurons (e.g., sensory neurons and motor neurons), myocytes (e.g., cardiac cells, skeletal cells, and smooth muscle cells), and endocrine cells (e.g., insulin-releasing pancreatic ß cells). In cases where the cell is a neuron, the neuron can be in the substantia nigra (e.g., in the pars *reticulata* of the substantia nigra). In some cases, the cell can be an excitable cell. In cases where the cell is a neuron, the neuron can be an excitatory neuron (e.g., neurons that release glutamate) or the neuron can be an inhibitory neuron (e.g., neurons that release GABA). A cell can be in vivo or ex vivo.

Inverted transporter polypeptides described herein (e.g., containing a leader sequence and a transporter protein), or nucleic acid encoding one or more inverted transporter polypeptides described herein, can be formulated into a composition (e.g., a pharmaceutically acceptable composition) for administration to a mammal (e.g., a mammal having or at risk for developing a disease or disorder characterized by altered cellular excitability). For example, a therapeutically effective amount of one or more inverted transporter polypeptides described herein a therapeutically effective amount of nucleic acid encoding one or more inverted transporter polypeptides described herein can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Inverted transporter polypeptides described herein (e.g., containing a leader sequence and a transporter protein), or nucleic acid encoding one or more inverted transporter polypeptides described herein, can be administered by any appropriate method. For example, a composition (e.g., a pharmaceutically acceptable composition) including one or more inverted transporter polypeptides described herein or nucleic acid encoding one or more inverted transporter polypeptides described herein, can be administered by any appropriate method. Inverted transporter polypeptides described herein, or nucleic acid encoding one or more inverted transporter polypeptides described herein, can be administered locally or systemically. Inverted transporter polypeptides described herein, or nucleic acid encoding one or more inverted transporter polypeptides described herein, can be administered by oral administration, parenteral administration (e.g., by injection such as intracranial injection, subcutaneous injection, intramuscular injection, intravenous injection, and intradermal injection), or inhaled administration. For example, a composition containing can be administered systemically by an oral administration to or inhalation by a mammal (e.g., a human). When being administered orally, a composition can be in the form of a pill, tablet, or capsule.

Inverted transporter polypeptides described herein (e.g., containing a leader sequence and a transporter protein), or nucleic acid encoding one or more inverted transporter polypeptides described herein, can be administered to a mammal having or at risk for developing a disease or disorder characterized by altered cellular excitability as a combination therapy with one or more additional agents/therapies used to treat a disease or disorder characterized by altered cellular excitability. In cases where one or more inverted transporter polypeptides described herein or nucleic acid encoding one or more inverted transporter polypeptides described herein are used in combination with one or more additional agents/therapies used to treat a disease or disorder characterized by altered cellular excitability, the one or more additional agents/therapies can be administered at the same time or independently. For example, the one or more inverted transporter polypeptides described herein or nucleic acid encoding one or more inverted transporter polypeptides described herein can be administered first, and the one or more additional agents/therapies administered second, or vice versa.

The invention will be further described in the following examples, which do not limit the scope of the invention described in the claims.

EXAMPLES

Figure 1B:
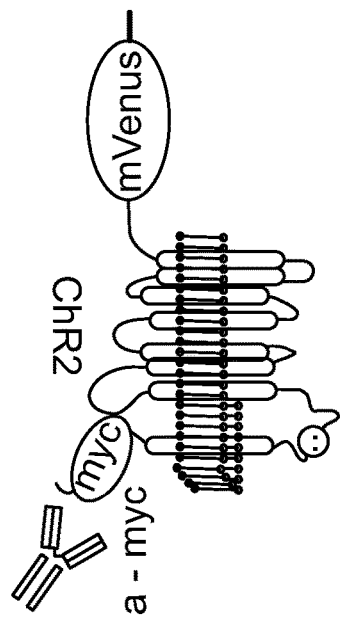
FIG. 1. A molecular engineering approach to topological inversion of rhodopsins. A, Schematic of the approach. Nx1B-TM denotes transmembrane domain of Neurexin 1B, ++denotes positively charged furin cleavage site. B, Immunocytochemical evaluation of the location of the N-terminal-myc epitope tag. Top: schematic of the approach. Bottom: Background-subtracted, bead fluorescence-normalized fluorescence intensity of regions of interest manually drawn over cell bodies. 1° Ab: primary anti-myc antibody. C, Proteinase-K-based evaluation of the location of the C-terminal-m Venus domain in primary neuronal cultures. Top: Schematic of the approach. Scissors depict action of extracellularly-added Proteinase K. Bottom left: Time-lapse live-cell imaging of four individual experiments. Scale bar: 1 µm. Bottom right: Background-subtracted change in fluorescence at the end of the assay (normalized to the starting fluorescence) for native ChR ET/TC (n=59), inverted ChR ET/TC (n=47), inverted CsChrimson (n=7) and inverted ArchT (n=6). D, Proteinase K-based evaluation of the location of the C-terminal m Venus domain for the fusion of *Drosophila melanogaster* OR 59D.1 gene N-terminal leader sequence and ChR ET/TC (n=42). Top: Schematic of the approach. Bottom: Background-subtracted change in fluorescence at the end of the assay. Error bars represent standard error of the mean.
Figure 1B:
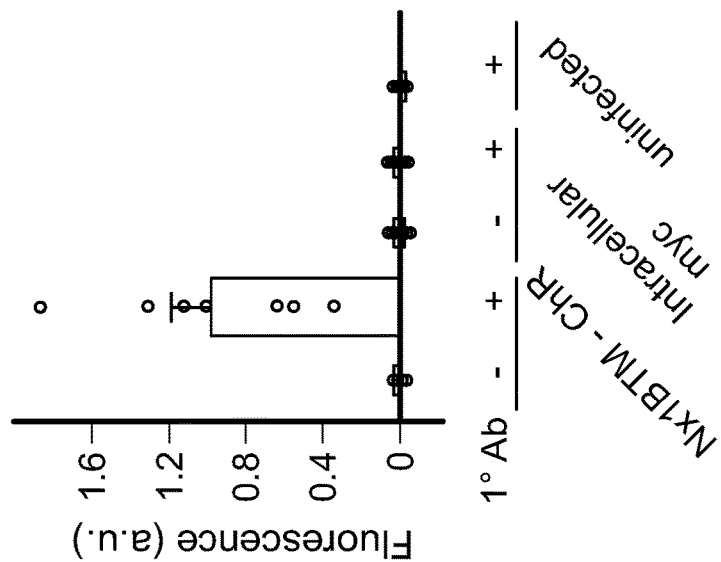
Figure 1A:
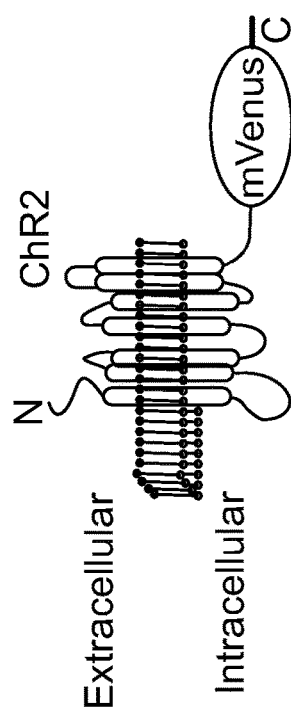
Figure 1A:
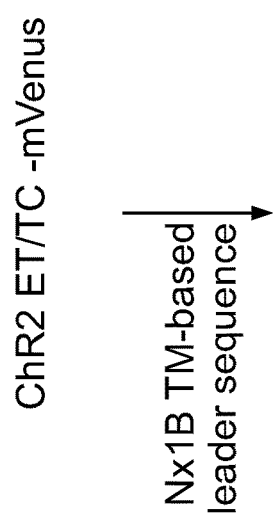
Figure 1A:
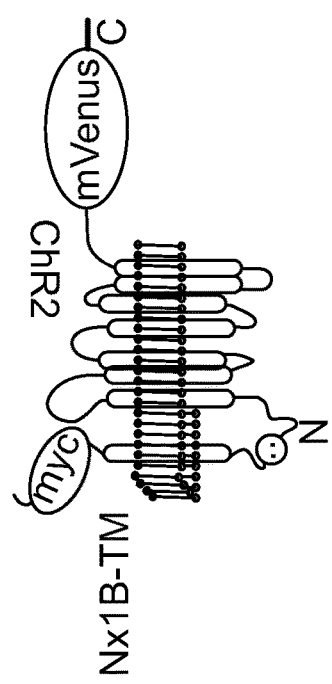

Example 1: Expanding the Optogenetics Toolkit by Topological Inversion of Rhodopsins Results To evaluate the potential of topological engineering for generating novel rhodopsin variants, a leader sequence containing the signal sequence and the transmembrane (TM) domain of Neurexin 1B-delta-a type-I integral membrane protein—was designed that could, in principle, impose topological inversion on any membrane protein with an extracellular N-terminus (FIG. 1A). To impart further stability on the orientation of the N-terminal TM domain, a short positively charged peptide was also included into the presumed cytoplasmic portion of the leader sequence. A positively charged peptide was chosen that serves as the recognition sequence for a Golgi-bound protease, furin, because establishing that the fusion protein is protected from furin-mediated cleavage would lend further support for the desired orientation of the leader sequence.

Figures 1C, 1D:
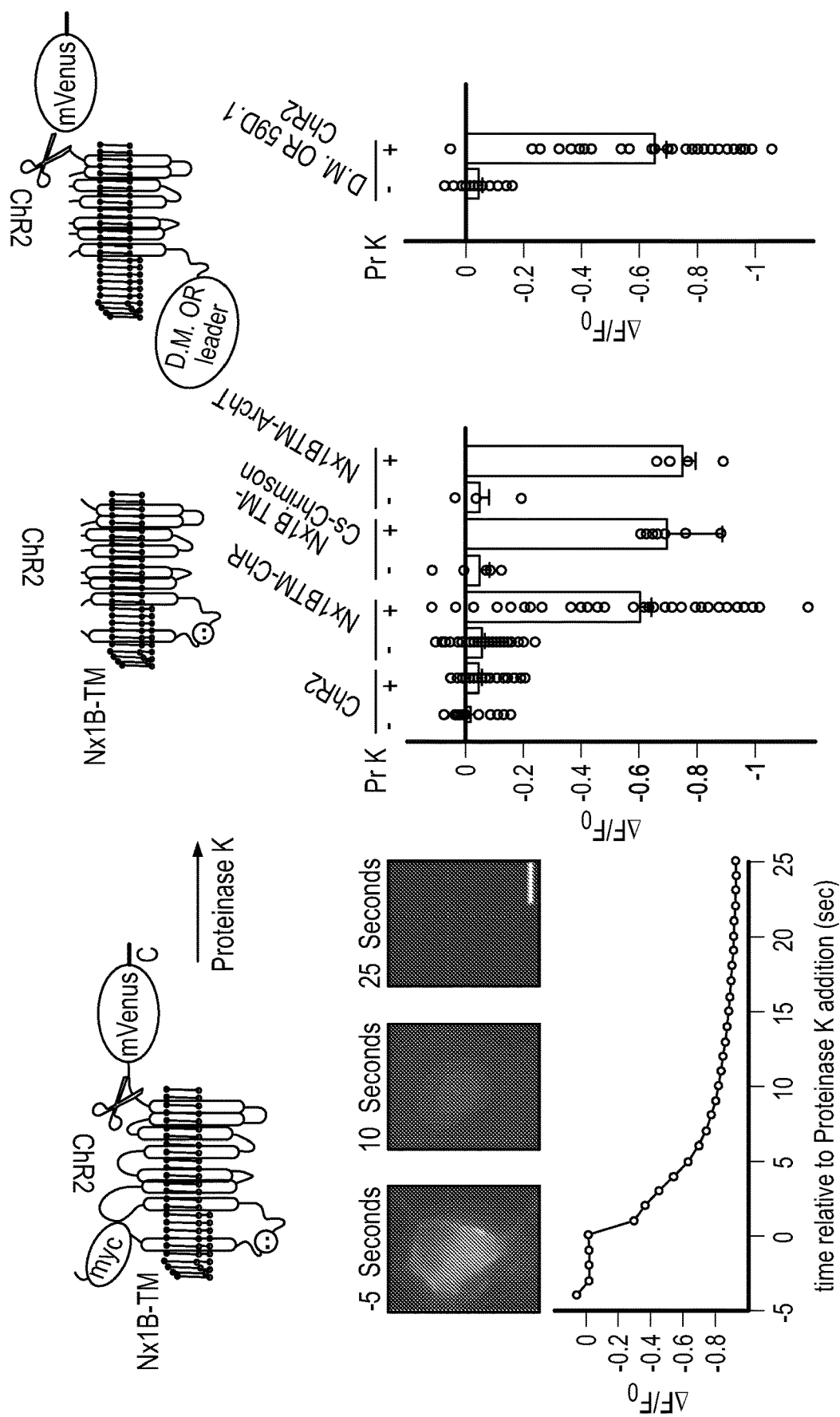
Figure 2A:
FIG. 2. Inverted ChR ET/TC displays robust intracellular trafficking. A, Image of a coronal rat brain slice with neurons in the cingulate cortex that project to supplementary motor cortex expressing Nx1B-ChR fusion. Note the evident fiber tracts suggestive of robust axonal trafficking. B, A maximum projection for a confocal image of rat layer V neuron expressing FLInChR with concentric circles at increasing radii describing the analysis of FLInChR expression as a function of distance from the soma center. C, Fluorescence intensity normalized to peak intensity along the circumference of concentric circles relative to the center of the soma. Only pixels from intersections of these circumferences and the segmented neuron are used. The red line represents the median fluorescence, blue boxes mark the 25th and 75th percentiles, whiskers represent the extreme data points and, + represent outliers. Note that despite a modest increase in the median fluorescence at the soma, the dendritic expression remains consistent throughout the neuron.
Figure 2B:
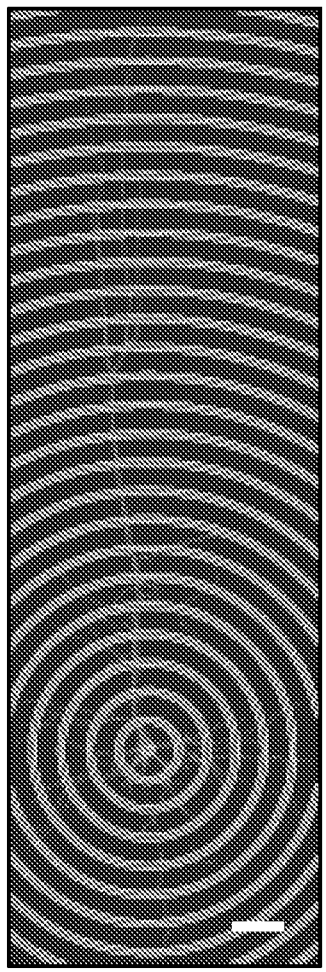
Figure 2C:
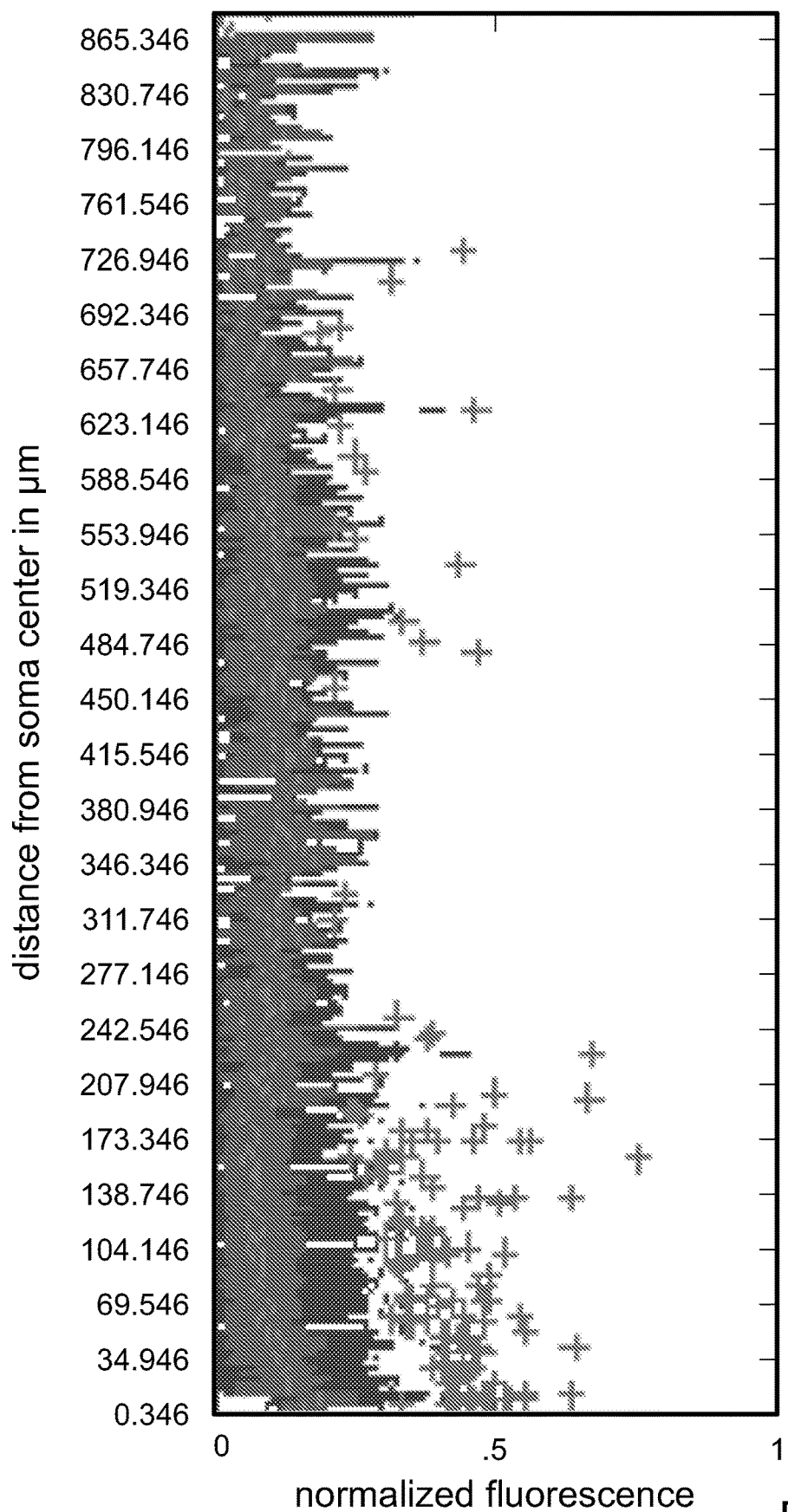
Figures 3, 4A:
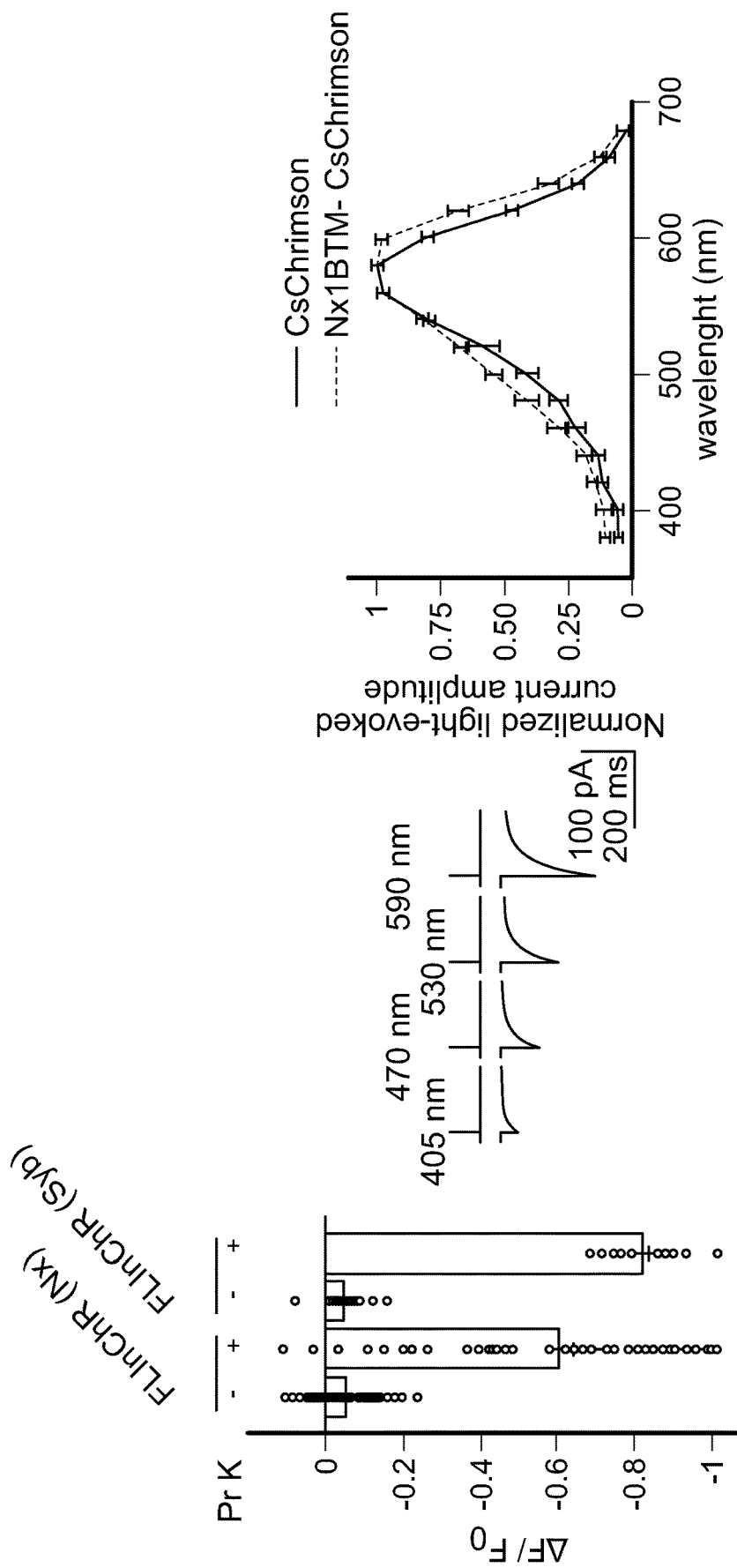
FIG. 3. Inversion is robust to the choice of N terminal linker domain. Proteinase-K-based evaluation of the location of the C-terminal-m Venus domain in primary neuronal cultures for FLInChR (Nx) (as in FIG. 1) and FLInChR (Syb) (n=16).

Fusion between the Neurexin (Nx)-based N-terminal domain and ChR2 E123T/T159C-a variant chosen because of its fast kinetics and robust membrane insertion-resulted in a protein that could be easily expressed at high levels, displayed efficient membrane targeting, and trafficked well down axons (FIG. 2). Immunostaining for the N-terminal myc-epitope tag under non-permeabilized conditions, and live-cell GFP florescence imaging in the presence of proteinase K, verified that both N- and C-termini of the fusion protein are in the extracellular space, as predicted for successful topological inversion (FIG. 1B, C). Pairing the Neurexin-based N-terminal domain with either CsChrimson or ArchT was equally effective at achieving inversion (FIG. 1C), as was pairing ChR E123T/T159C with an alternative N-terminal domain that contained the transmembrane domain of Synaptobrevin (Syb) (FIG. 3).

Whether any naturally existing non-canonical orientation of a transmembrane protein may be attributed to its N-terminal domain was explored. Insect odorant receptors—a family of heptahelical proteins that have the opposite membrane orientation compared with their mammalian counterparts, and function as odor-gated ion channels rather than G-protein coupled receptors—were focused on. Strikingly, fusion of the N-terminal leader sequence from the *Drosophila* OR 59D.1 gene to ChR E123T/T159C also resulted in an inversion (FIG. 1D). This finding lends further credence to the notion that introduction of targeted N-terminal domains through recombination may have contributed during evolution to changes in membrane protein orientation, and possibly to the emergence of new functionalities.

To evaluate the functional consequences of topological inversion, the current evoked by photoactivation of the inverted proteins in cultured hippocampal neurons (transfected at DIV7, evaluated at DIV 14-21) was examined. Flipping the orientation of CsChrimson in the membrane preserved the inward direction of the photocurrent at resting membrane potential and had no significant effect on the current's spectral sensitivity (FIG. 4A). The photocurrent still reversed when the membrane was depolarized (FIG. 4B). However, the reversal potential of the inverted CsChrimson was significantly lower than that of the original opsin ($-35.3+5.2$ mV, n=5 vs $4.7+2.5$ mV, n=5, p<0.0001). Decreasing the extracellular Na+ concentration from 130 mM to 5 mM caused a further leftward shift in the reversal potential (to $-62.7+3.6$ mV, n=5, p<0.001 vs 130 mM Na+), bringing it closer to the reversal potential for K+. Together, these results indicate that for CsChrimson, topological inversion preserved the opsin's cation channel-like properties but led to a significantly (~7-8 fold) increased K+ permeability—a sought-after functional change that has eluded other molecular engineering efforts.

Inversion of ChR E123T/T159C led to an even more dramatic change in opsin functionality. Cells expressing inverted ChR E123T/T159C FLInChR variants displayed robust outward currents suggesting that inversion converted this opsin from a potent activator into an inhibitor (FIG. 4C). Comparison of current amplitudes elicited by photostimulation at varying wavelengths revealed that the spectral response of FLInChR photocurrents was red-shifted with respect to its 'topological isomer', peaking around 560 nm (FIG. 4D). FLInChR photocurrents were outward at all tested membrane potentials and exhibited a very weak voltage dependence regardless of the internal solution used, implicating a pump-like mechanism for FLInChR conductance (mean increase of 18+4% at +40 mV compared to $-80$ mV, n=16, FIG. 4C). Replacement of external ions with sucrose had no effect on FLInChR photocurrent amplitude (p=0.5, n=4, FIG. 4E), indicating that FLInChR photocurrents result from transport of cations out of the cell. An ammonium pre-pulse protocol (Schwiening and Boron, 1994) designed to shift the cell's pH-first basic, and then acidic-had no effect on current amplitude (FIG. 4F, n=5, p=0.9), suggesting that protons are not the exclusive charge carrier of the FLInChR photocurrent. Similarly, no change in photocurrent amplitude was detected when switching between Na+ and K+-based internals (FIG. 4G, n=9 vs n=22, p>0.5). Nevertheless, increasing cation size further by substituting with TEA+-based internal resulted in a significant drop in the photocurrent (FIG. 4G, 165+22 pA for K+, n=22 vs 106+15 pA for TEA+, n=20, p<0.05, one-way ANOVA with a post-hoc Tukey's test). Taken together, the above evidence is most consistent with the notion that topological inversion has transformed ChR2 E123T/T159C into a potent optogenetic inhibitor that functions like a light-activated, non-selective cation pump. Thus, topological inversion can indeed be sufficient to produce marked changes in the functional properties of opsins. Moreover, similarly to the case of CsChrimson inversion, inversion of ChR E123T/T159C resulted in a functionality (cation pumping) distinct from those attained with previous molecular engineering efforts. This finding, together with the observation that inversion also markedly altered the action spectrum of ChR2 ET/TC (FIGS. 4D), suggests that topological engineering induces a significant rearrangement of side chains around the active site.

The efficiency of optogenetic-based manipulations of cell activity critically depends both on the properties of the opsin as well as the biophysics of the targeted cell type. Thus, it is desirable to have a range of properties (different ions conducted, a continuum from pump-like to channel-like behavior, etc.) for specific use cases. However, to qualify as a viable optogenetic tool for neuroscience a reagent must be capable of dramatically perturbing activity in at least some cell types. To verify that the altered active site packing of the inverted configuration is not incompatible with sufficient light-dependent ion transport for robust circuit interrogation inhibitory potential of FLInChR variants in brain slices was evaluated. Substantia nigra pars *reticulata* (SNr) neurons were targeted due to extensive prior experience using the parent ChR2 variant in this experimental preparation (see, e.g., Brown et al., Elife 3: e02397 (2014)) and the that fact that tonically active neurons provide an ideal test case for evaluating inhibitory optogenetic actuators.

Figure 5A:
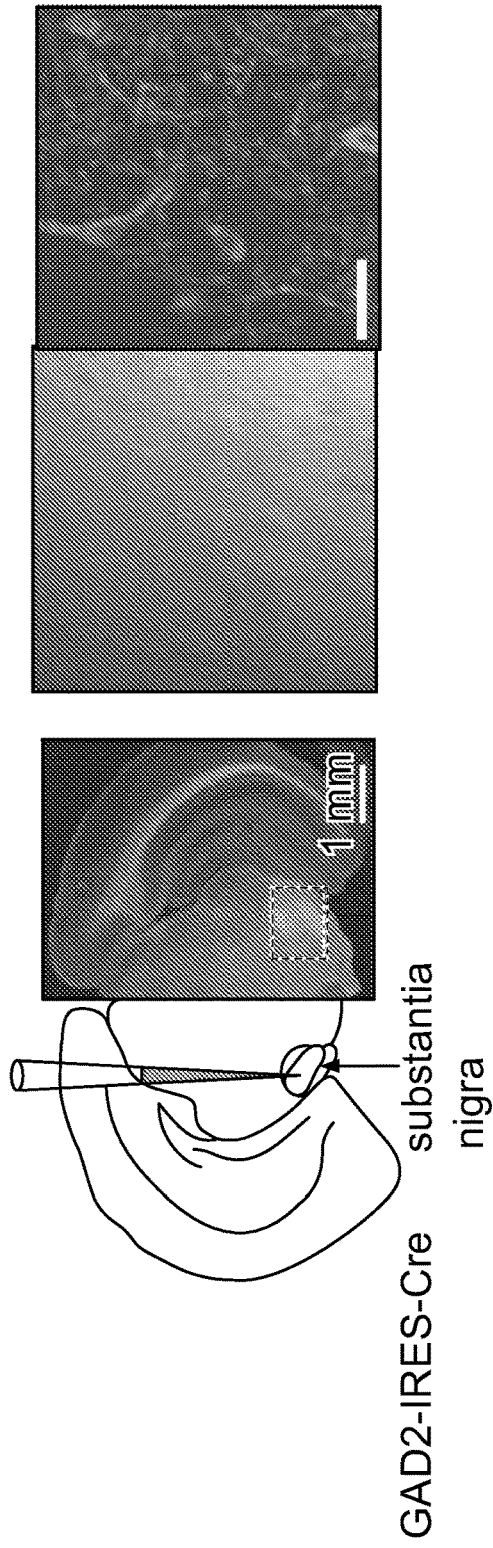
FIG. 5. Opsin inversion is compatible with regular ionic flux. A, Left: Schematic of the experimental preparation. Brain slices were prepared from GAD2-IRES-Cre mice that had been previously injected into substantia nigra with AAV2/1 CAG FLEX FLInChR-m Venus or AAV2/1 CAG FLEX ArchT-mVenus. Right: representative differential interference contrast (DIC) and fluorescence images of FLInChR-expressing slices. B-D, Left two panels: Representative whole cell currents observed in SNr cells expressing either FLInChR (Nx) (B), FLInChR (Syb) (C) or ArchT (D) held at −70 mV in response to a 1 ms light pulse (10 mW/mm2 at the focal point of the objective) at 470 nm and 590 nm. Right two panels: Photocurrent amplitude as a function of light power at the objective (n=4 cells each). Light shading represents standard error of the mean. E-G, Top: Response latencies across cells for the two wavelengths. Bottom: Decay constants for light-induced currents (n=4 cells each). Error bars represent standard error of the mean.
Figure 5B:
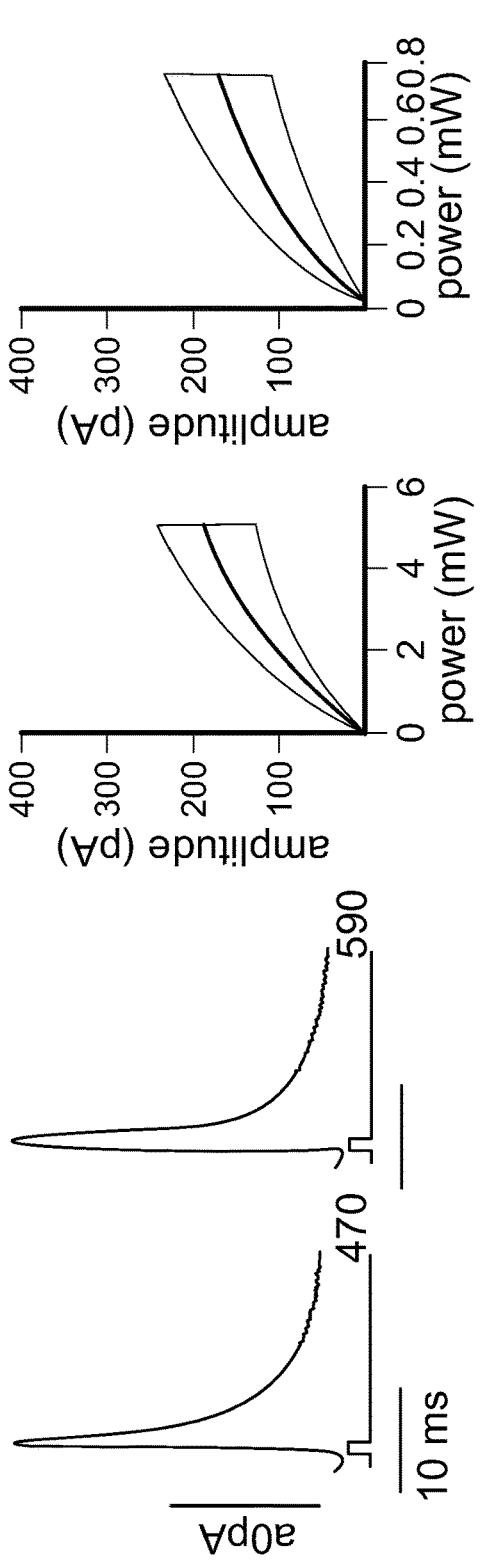

Midbrain slices were prepared from adult GAD-Cre mice that had been injected into SNr with an adeno-associated virus carrying m Venus-tagged FLInChR or ArchT and targeted for whole cell recordings SNr GABAergic neurons visually identified to express the opsin (FIG. 5A). To further ascertain that inversion resulted in a marked change in the opsin function as well as to detect any contribution from potentially native, un-flipped ChR, conditions (wide-field illumination with a 1 ms pulse of 470 nm light; holding potential of $-70$ mV) that have been shown to elicit strong inward currents in ChR2-expressing SNr GABAergic cells were chosen (see, e.g., Brown et al., Elife 3: e02397 (2014)). FLInChR-expressing cells displayed robust outward currents under these conditions (FIG. 5B for FLInChR (Nx) and FIG. 5C for FLInChR (Syb)). Consistent with the observations in dissociated cultures, FLInChR-mediated photocurrent was observed even when cells were stimulated with 590 nm light (FIG. 5B, C)—conditions under which the parent ChR2 variant is not expected to display robust activity (Berndt et al., Science 344:420-424 (2011)). Evoked outward currents were on par with those mediated by ArchT—a commonly used and potent optogenetic inhibitor (FIG. 5D). A similarly rapid onset latency (FLInChR (Nx): 0.33+/−0.01 ms @ 470 nm; 0.30+/−0.01 ms @ 590 nm, n=4, FIG. 5E, top panel; FLInChR (Syb) 0.24+/−0.01 ms @ 470 nm; 0.24+/−0.01 ms @590 nm, n=4, FIG. 5F, top panel; ArchT: 0.25+/−0.04 ms @ 470 nm; 0.22+/−0.03 ms @ 590 nm, n=4, FIG. 5G, top panel) and rapid decay time constants (FLinChR (Nx): 2.51+/−0.14 ms @ 470 nm; 2.60+/−0.25 ms @ 590 nm, n=4, FIG. 5E, bottom panel; FLInChR (Syb) 3.07+/−0.13 ms @ 470 nm; 3.31+/−0.24 ms @590 nm, n=4, FIG. 5F, bottom panel; ArchT: 2.49+/−0.04 ms @ 470 nm; 2.24+/−0.03 ms @ 590 nm, n=4, FIG. 5G, bottom panel) were observed for FLInChR- and ArchTmediated currents. The comparable performance of Arch and FLInChR variants argues that the structural re-arrangements in the vicinity of the active site (a consequence of inversion) are compatible with efficient light-dependent ion transport.

Figure 6B:
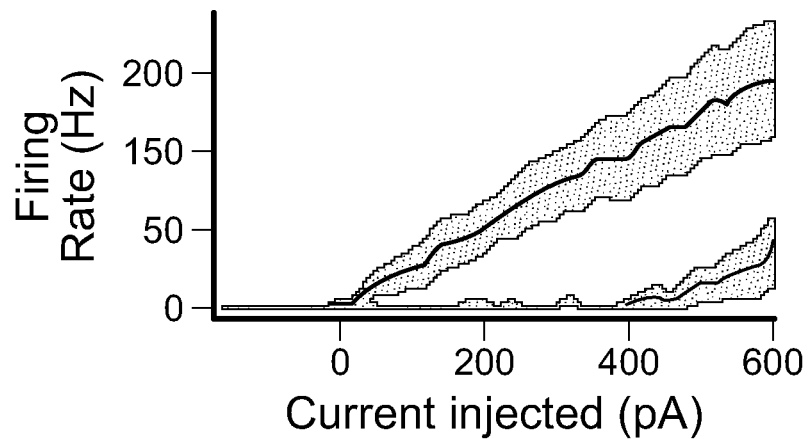
FIG. 6. FLInChR mediates efficient suppression of spiking. A, Example responses of a FLInChRexpressing SNr cell to step current injections with and without 470 nm light (10 mW/mm2 at the focal point of the objective). Top: overlaid voltage traces. Bottom: raster plots of spiking activity. B, Population average of firing rates in response to injected current with (black) and without (blue) light exposure. C, Spiking activity of an example cell in the presence of progressively longer illumination at 470 nm.
Figure 6C:
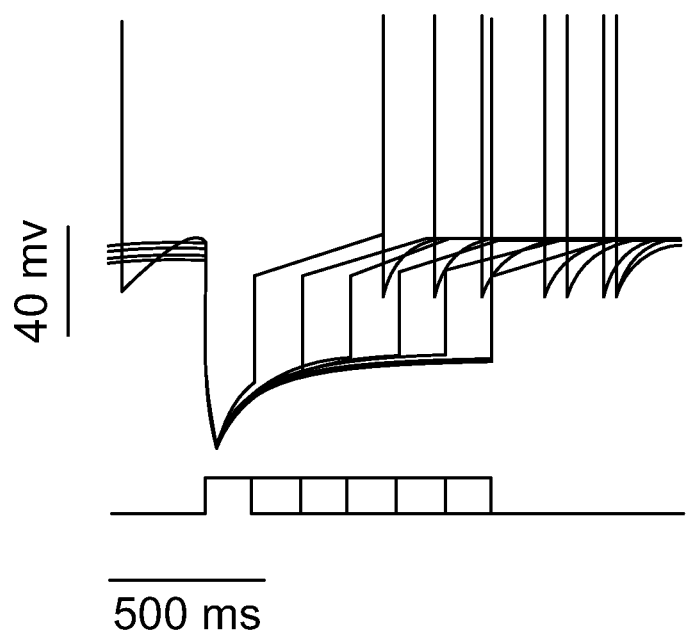
Figure 7A:
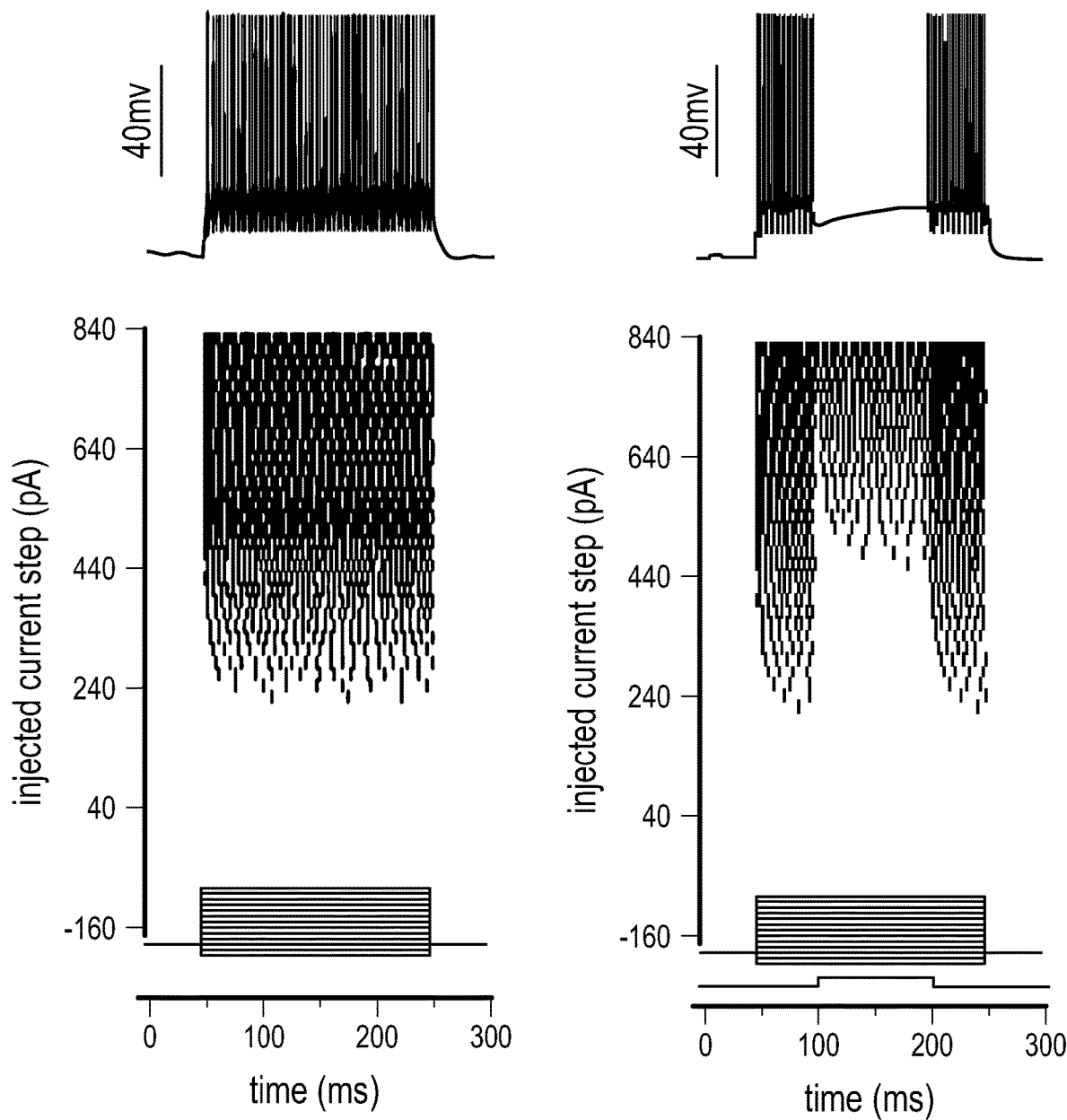
FIG. 7. FLInChR mediates efficient suppression of spiking in cortical neurons. A, Responses of a FLInChR-expressing layer 4 stellate cell to step current injections with and without 470 nm light. Top: overlaid voltage traces. Bottom: raster plots of spiking activity. B, Left panel: Firing rate in response to injected current of different amplitude with (black) and without (blue) light exposure. Right panel: Percent inhibition for different levels of injected current.
Figure 7B:
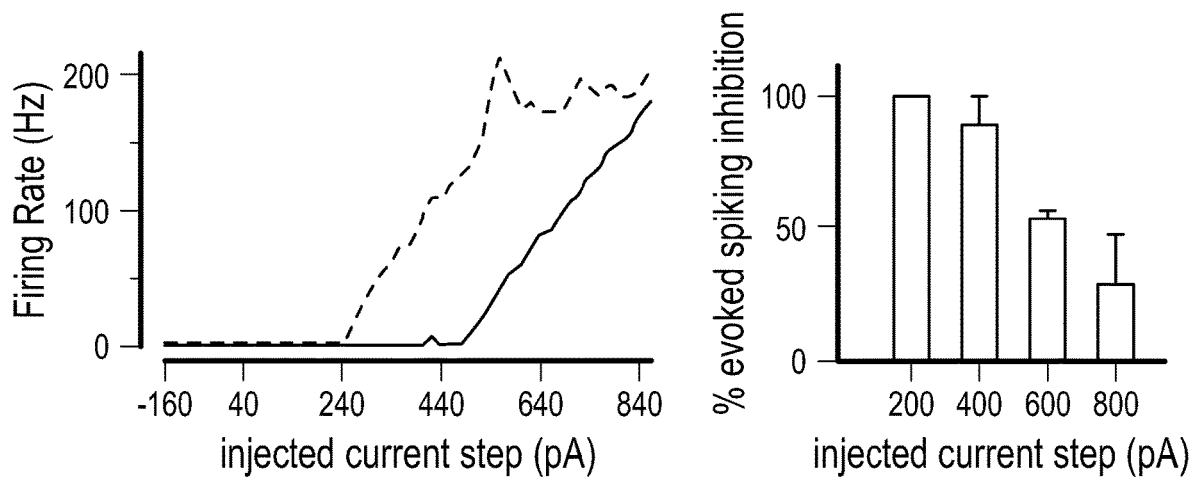
Figure 8:
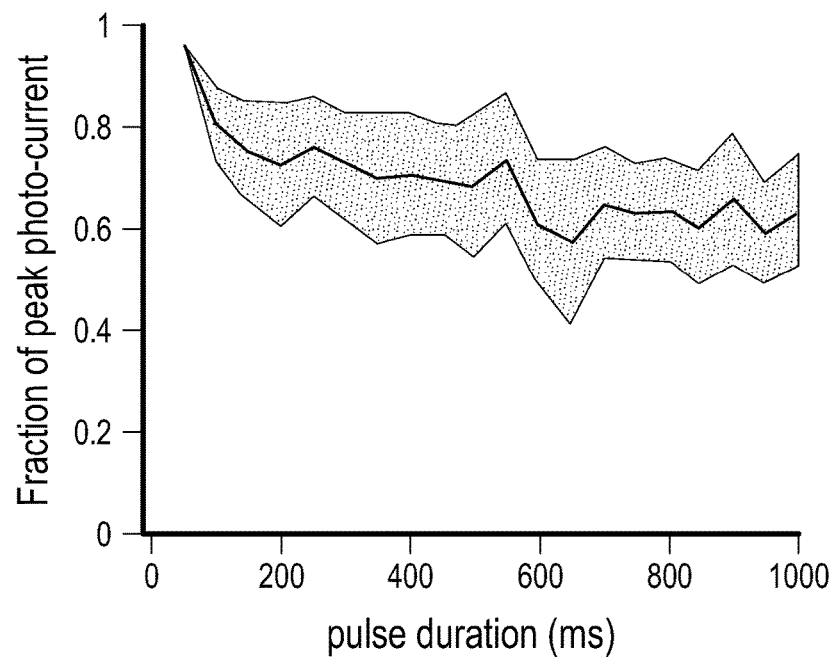
FIG. 8. FLInChR-mediated photocurrent shows moderate desensitization. Voltage clamp recordings from FLInChR-expressing SNr neurons (n=4) with long light pulses. Note only moderate decay of photocurrent after the initial 100 ms. Light shading represents standard error of the mean.

The fact that SNr GABAergic cells respond to depolarizing current in vitro with firing rates of over 150 Hz (FIG. 6A) was used to examine the efficiency, with which FLInChR can inhibit evoked activity. In the absence of light stimulation, it was possible to evoke progressively higher spiking frequency in FLInChR-expressing neurons by injecting increasing steps of depolarizing current in a whole-cell current clamp mode. Brief pulses (100 ms) of photo-stimulation induced significant hyperpolarization of the membrane voltage that was maintained even during depolarizing current injection steps. Evoked spiking was mostly eliminated during photostimulation, and could only be partially recovered with very large (>400 pA) current injections (FIG. 6A, B). Similarly, efficient suppression of evoked spiking was observed in FLInChR-expressing cortical neurons (FIG. 7). The ability to sustain photoinhibition for prolonged periods (FIG. 6A, C) was likely due to only moderate desensitization of FLInChR-mediated currents beyond the initial 100 ms (FIG. 8, photocurrent amplitude normalized to peak: 0.8062+/−0.0743 at 100 ms, 0.6333+/−0.1131 ms at 1000 ms, n=4). Combined, these results demonstrate that FLInChR is a robust optogenetic inhibitor that can suppress evoked activity even in fast spiking neurons and may be sufficient for in vivo circuit interrogation experiments in behaving animals.

Figure 9E:
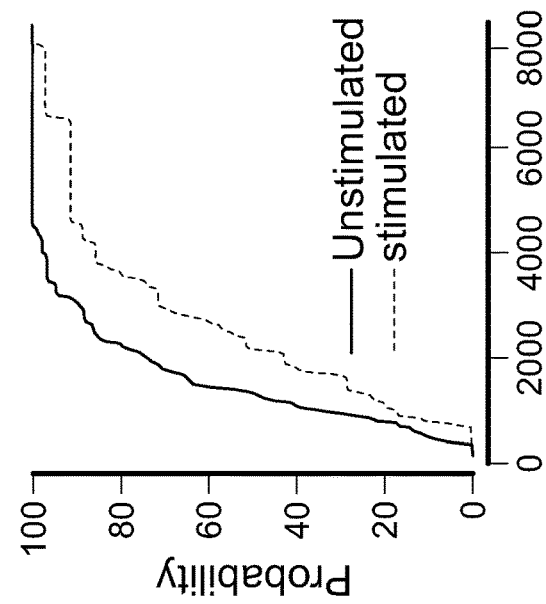
FIG. 9. FLInChR is an effective light-dependent inhibitor for circuit dissection. A, Experimental paradigm used to evaluate the efficacy of FLInChR in awake behaving animals. Head-fixed mice were trained to manipulate a joystick, with responses above a certain threshold preferentially rewarded. Effect of FLInChR-based perturbation of neural ensemble activity in SNr on response vigor was then assessed. Selective expression of FLInChR in the GABA-ergic cells of the SNr was achieved through stereotaxic delivery of AVV2/1 FLEX-FLInChR in GAD2-IRES-Cre mice. B, Schematic of the experimental protocol. Trial start (green diamond) was un-cued. Reaches had to pass variable threshold (gray diamond) for a delayed water reward (blue square). Reaches were extracted using both the Euclidean displacement and the velocity of the joystick. Light (473 nm, 1-5 mW at the fiber tip) was delivered on the first reach of approximately 20% of trials. C, Instantaneous velocity and trajectory in space for an example reach before (light gray), during (blue) and after (dark gray) light delivery. D, Duration of 'stimulated' reaches as a function of the fraction of reach completed at the time of light onset (n=627 reaches in 6 animals). E, Cumulative distribution of durations for 'stimulated' (n=25) and 'unstimulated' (n=94) reaches during one session. F, Mean reach durations for 'stimulated' reaches than for 'unstimulated' reaches across 23 sessions in 6 animals. *, p<0.01, paired t-test. G, Distribution of reach durations for all 627 'stimulated' and 2254 'unstimulated' reaches. White dot indicates distribution median, black-distribution mean. *, p<0.01, Mann-Whitney test. H, Schematic of the experiment aimed to optogenetically tag projection neurons in behaving mice and rats. I, Top two panels: Activity in an example rat cortico-striatal neuron for 800 repeated light presentations. Light power was 2 mW at the fiber tip. Bottom panel.
Figure 9F:
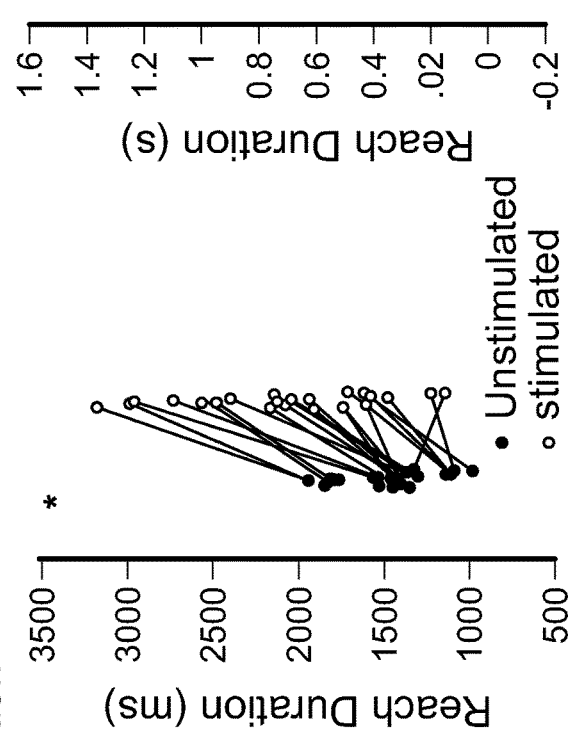
Figure 9D:
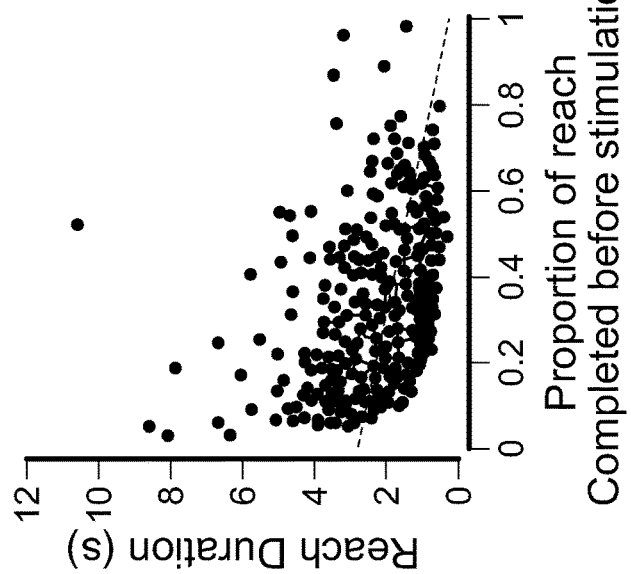

SNr neurons are the primary output of basal ganglia in rodents—a brain structure thought to be central to the bi-directional control of the vigor of voluntary movement in rodents, and primates. Given the efficacy of FLInChR in vitro whether focal optogenetic inhibition of SNr projection neurons could be used for behavioral circuit perturbation experiments was examined. Mice expressing FLInChR in the SNr were trained on a previously developed effort-based operant task that requires animals to adjust the vigor of a reaching movement to obtain reward (FIG. 9A, B). Once animals attained expert performance, activity in the SNr was suppressed on 25% of randomly selected reaches by delivering light through bilaterally implanted optical fibers. The perturbation was applied selectively during movement. Consistent with the efficient perturbation of spiking observed in FLInChR-expressing animals in vitro, a specific and systematic reduction was observed in peak velocity of reaches in "light ON" trials (FIG. 9C) which necessitated reaches of significantly longer reach duration for all mice (FIG. 9D-G). Importantly, the size of the observed behavioral effect for FLInChR-mediated SNr perturbation of movement vigor was similar in magnitude to that observed in other experiments where basal ganglia activity was manipulated with Arch in this task (Panigrahi et al., ('el/162:1418-1430 (2015)) as well as other prior measurements. Thus, although comparisons between different optogenetic tools are notoriously subject to the vagaries of the specific experimental preparation, the observed robust performance places FLInChR variants favorably amongst extant optogenetic tools for in vivo circuit perturbation experiments. Indeed, parallel sets of behavioral perturbation experiments in *Caenorhabditis elegans* nematodes expressing FLInChR in muscle cells (FIG. 8), demonstrating muscle inhibition and body elongation, and in rats expressing FLInChR in prefrontal cortical neurons (not shown), provided further support that this new opsin variant is a powerful new inhibitor suitable for in vivo manipulations.

The rapid kinetics of FLInChR-mediated photoinhibition evident in slice experiments (FIG. 5) prompted us to investigate whether FLInChR might aid with optogenetic tagging efforts—a common method for identification of neuronal cell types in electrophysiological experiments. While simple in principle, such experiments can be notoriously difficult in awake, active animals because of pronounced network effects, especially in circuits with strong recurrent connectivity, e.g. neocortex. The depolarizing opsin ChR2 is by far the most frequently used optogenetic tag, but in excitatory neuronal populations, its use for opto-tagging can be problematic (see, e.g., Lima et al., PloS one 4: e6099 (2009)). As latencies of light-driven modulation are often on par with synaptic delays, light-dependent activation by neighboring ChR2+ neurons driving a ChR2-cell over threshold can be indistinguishable from direct light activation of a ChR2+ cell. Inhibitory opsins, in principle, provide an alternative approach to optotagging populations of excitatory cells such as cortical projection neurons (PNs). Since PNs derive most of their excitatory drive from long-range inputs (Guo et al., 2017), short latencies to light-dependent inhibition is unlikely to result from removal of synaptic drive through local recurrent connections. Therefore rAAV2-retro-mediated delivery was used to selectively target long-range PNs in layer 5 of sensorimotor cortex in awake, behaving mice and rats, and analyzed the distribution of latencies to detectable photoinhibition through simultaneous extracellular recordings (FIG. 9H).

Figure 9I:
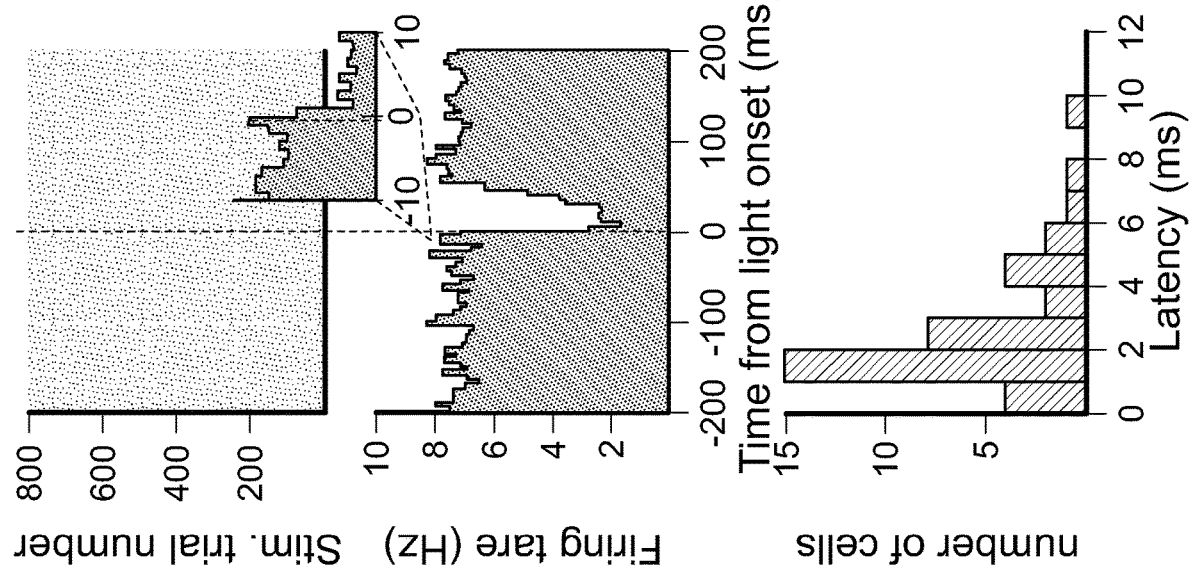
Figure 9G:
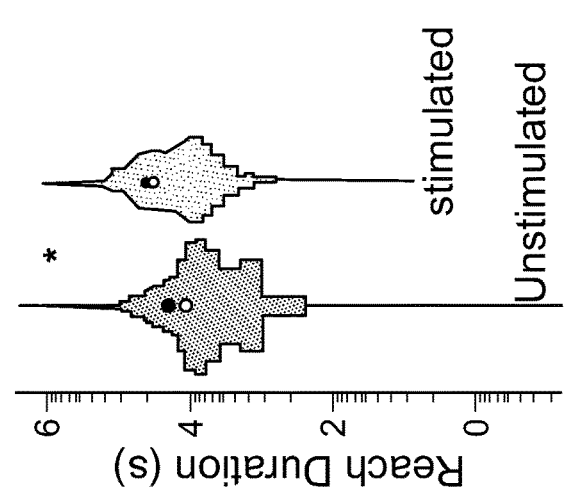
Figure 9H:
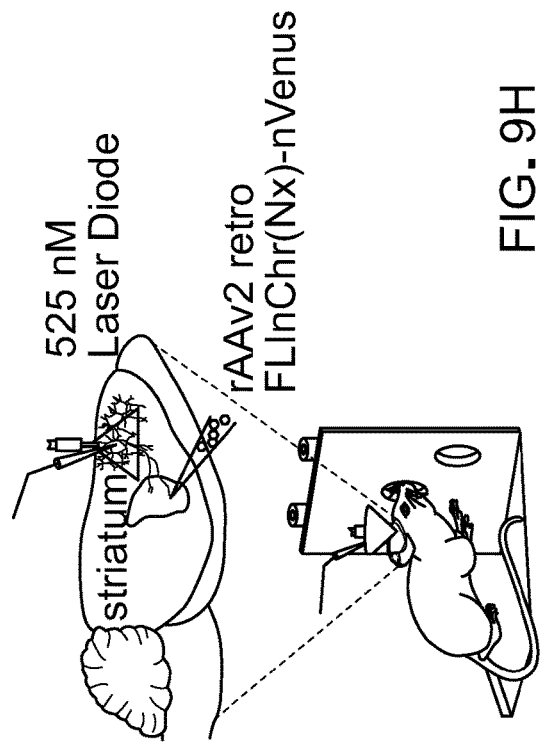
Figure 9J:
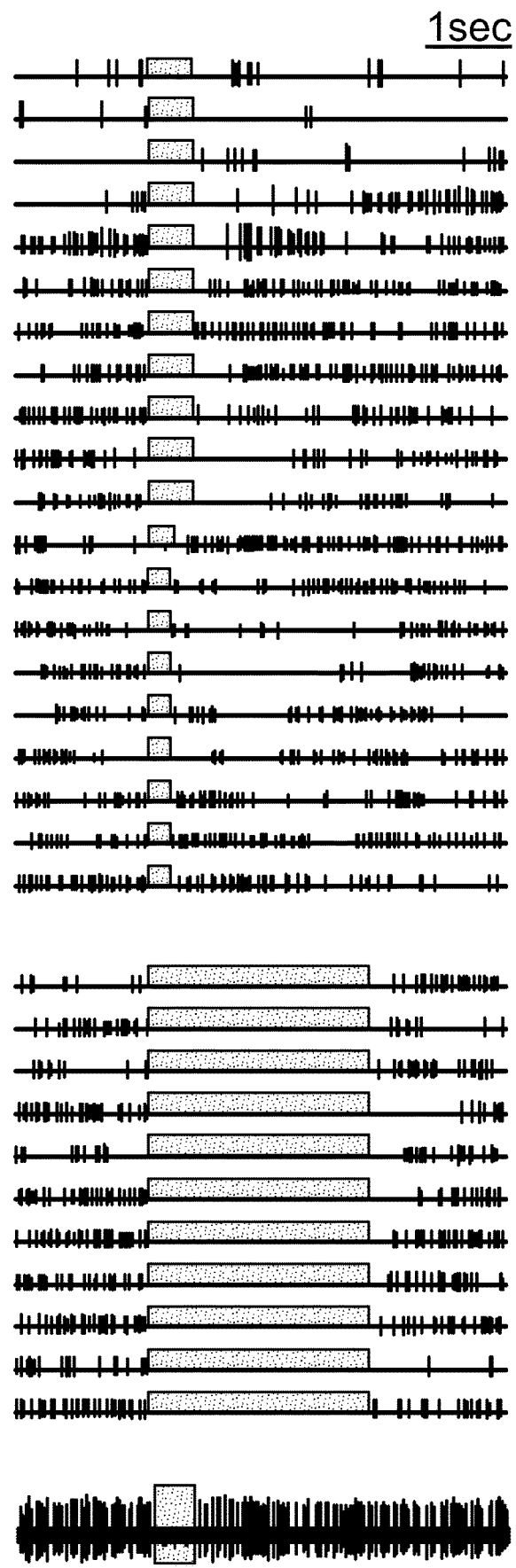
Figure 9K:
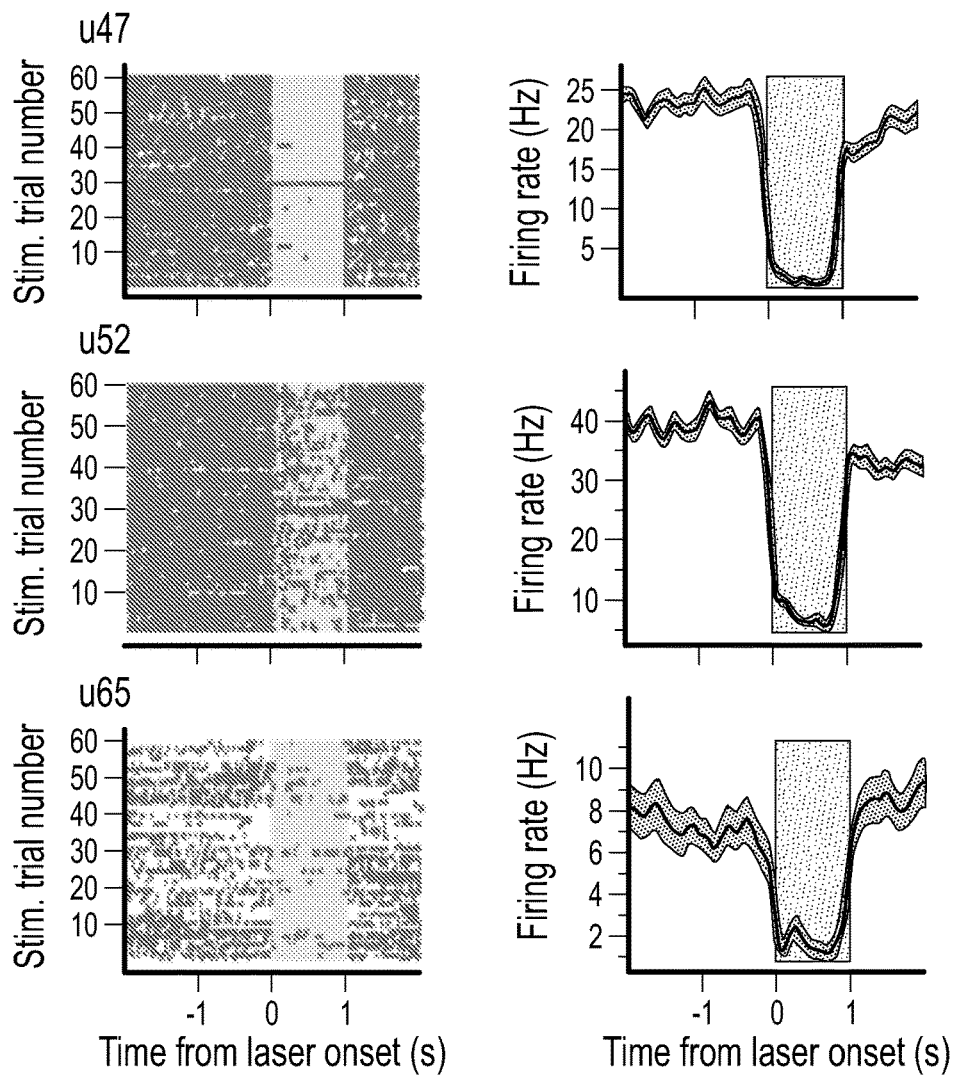
Figure 9L:
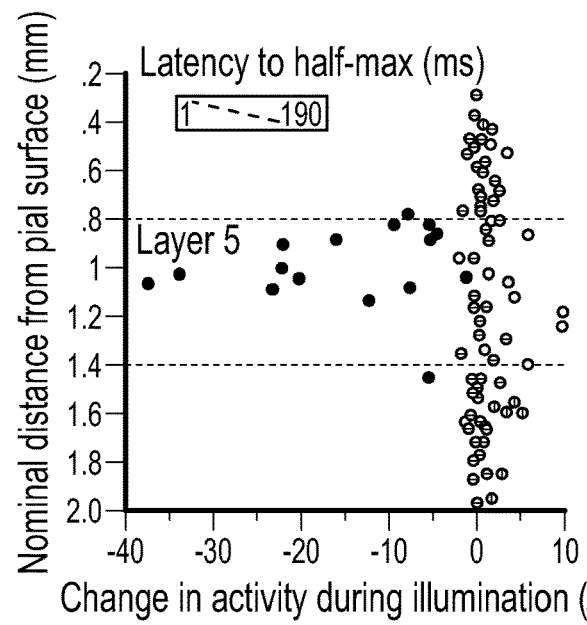

Robust photoinhibition was easily observed even in large rat PNs after 2 to 3 weeks of expression (FIG. 9I, significant responses detected in 19.5% of recorded units). When the optical fiber was advanced alongside the recording electrodes, the majority of light-sensitive units displayed latency to photoinhibition below three milliseconds (although latencies up to ten milliseconds could be observed in some cases). The ease of finding units with very short photoinhibition latencies and their spatial distribution (nominal depths of 0.9 to 1.3 mm from the cortical surface, consistent with the location in the rat brain of retrogradely-labeled striatal-projecting cortical neurons) strongly suggests that short-latency suppression is mediated by a direct effect. To verify the efficacy of direct FLInChRmediated photo-inhibition in such settings, juxta-cellular recordings were used in the equivalent experiment in the mouse. Illumination through the pipette was sufficient to induce rapid suppression of activity that could be maintained for up to 5 seconds of constant illumination (FIG. 9J), further arguing in favor of the direct nature of the observed photoinhibition. Moreover, when activity across all cortical layers was evaluated simultaneously with a large, high channel-density electrode array, units with rapid and robust suppression of firing (FIG. 9K) were exclusively found at depths consistent with layer 5 PNs (FIG. 9L). Interestingly, these high-density recordings revealed that targeted photoinhibition of targeted PNs is accompanied by dis-inhibition of other cortical neurons within the circuit (FIG. 9L, units with positive change in activity during illumination). However, the observed positive modulation of activity was both systematically delayed compared to presumed direct photoinhibition (indicative of poly-synaptic connectivity) and distributed across cortical layers. Collectively, these data suggest that FLInChR can be used in vivo in awake animals to effectively silence target populations of neurons. Moreover, the magnitude, speed and duration of activity suppression attainable even in large, difficult-to-inhibit pyramidal neurons argue that FLInChR is a useful tool for a variety of perturbation and opto-tagging experiments.

Methods

Dissociated Neuronal Cultures

Dissociated hippocampal cultures were prepared from Sprague-Dawley post-natal day 0 to 1 rat pups. Fourty-thousand neurons were plated on each poly-D-Lysine coated glass coverslips (Cat no. 3524; Corning) and cultured in in NBACTIVE4 (BrainBits).

Constructs and Adeno Associated Virus

TABLE 1

Viruses and payloads

| Serotype | Payload | Titre (GC/mL) |
|---|---|---|
| AAV2/1 | CAG-hChR2(ET/TC)-mVenus | 2.3E+12 |
| AAV2/1 | CAG-Nx1BTM-FCS-ChR2(ET/TC)-m Venus | 1.9E+12 |
| AAV2/1 | CAG-Flex-CsChrimson(TR)-mEGFP | 8.8E+12 |
| AAV2/1 | CAG-Nx1BTM-CsChrimson (CORRECT ME) | 2.8E+12 |
| rAAV2-retro | CAG-Cre | 7.1E+12 |
| rAAV2-retro | CAG-Flex-Nx1BTM-ChR2ET/TC-m Venus | 3.0E+12 |
| AAV2/1 | CAG-Nx1B TM-ARCH(TR)-mEGFP | 1.6E+12 |
| AAV2/1 | CAG-Cre | 1.1E+12 |
| AAV2/1 | CAG-FLInCHR (Syb)-m Venus | 2.1E+12 |
| AAV2/1 | CAG-Flex-FLInCHR(Syb)-m Venus | 2.0E+12 |

Proteinase K Assay

Coverslips of dissociated hippocampal neuronal cultures were infected with AAVs (see above) seven to ten days after plating. Seven to ten days after AAV infection, coverslips were transferred into a 24 well glass bottom plate (Cat no. P24G-1.0-13-F; Matek Corp) with 80 µl to 100 µl of DPBS with $Ca^{2+}$ and $Mg^{2+}$ (Cat no. 14040117; Gibco) in each well. Epifluorescence imaging was performed using an Olympus x81 microscope equipped with a 40X objective (Olympus UplanFLN 40x/0.75) and FITC cube (FITC-2024B-000; Semrock) using Slidebook 5.0-Innovatove Application (in-telligent-imaging.com). Images were acquired at a rate of 1 Hz for 30 seconds. Following the acquisition of five baseline images, either 40 µl of PBS (vehicle) or 40 µl of 2.3 mg/mL proteinase K (1:10 dilution of 1095 units/mL or 23 mg protein/mL, Sigma Cat No P4850) was added to the well, and twenty-five additional images were acquired.

Time-lapsed images were analyzed using custom Matlab and Python scripts. Regions of interest (ROI) and background regions were manually selected using the first image from each experiment, blind to the condition. The difference of the mean fluorescence of each ROI and the mean fluorescence from the background region in the same image was calculated, and the mean of these differences for the five baseline images ($F_0$) and the five final images ($F_{final}$) determined. Using this initial and final fluorescence, a difference in fluorescence was found and normalized to the initial fluorescence to yield the normalized change in fluorescence (AF/Fo).

Myc-Tag Assay

Neurons were infected five days post plating with AAV-CAG-Flincher-m Venus and AAV-CAG-Myc-GFP. Ten days post infection three wells in each group were stained with rabbit anti-c-myc primary antibody (C3956; Sigma) at 1:1000 dilution for 60 minutes. Wells were washed with PBS 3 times, and then fixed with 4% paraformaldehyde (PFA) in 0.1M phosphate buffer (PB). All of the wells were labeled with Goat anti-Rabbit IgG secondary antibody Alexa Fluro 594. Ultra Rainbow Fluorescent Particles Beads (Cat #610; mean diameter: 3.80 µm; Bangs Laboratories, Inc.) were diluted 1:500 for imaging. Images were acquired for a single time point using microscopy setup described above, with addition of imaging Alex Fluor 594 using a TRITC filter set (TRITC—B-OMF-Samrock).

Each image was analyzed blind to condition, by selecting regions of interest (ROI) for the soma, background and bead regions for each coverslip and the mean fluorescence for each ROI determined. The background ROI mean fluorescence was subtracted from the mean soma ROI fluorescence, and then normalized to the mean bead fluorescence to yield the arbitrary units (a.u.) in FIG. 1.

In Vitro Whole-Cell Electrophysiology in Dissociated Neuronal Cultures

In vitro electrophysiological characterization of opsins was done in hippocampal neurons cultured prepared as described above and infected with a virus carrying the payload of interest at 7 days in vitro (DIV). At 14-21 DIV, whole cell recordings were done using an extracellular solution of artificial cerebrospinal fluid (ACSF) that contained the following: 135 mM NaCl, 15 mM glucose, 3 mM KCl, 1.3 mM $CaCl_2$), 1 mM $MgSO_4$, 10 mM HEPES. For wholesale external ion replacement experiments (FIG. 4c) and well as reductions in [Na] (FIG. 5b), ions were replaced with equimolar amounts of sucrose. SR95531 (5 µM) and Kynurenic acid (0.1 mM) were added to all solutions to block ionotropic GABA and glutamate receptors, respectively. All experiments were done at room temperature, which was approximately 25° C. Glass recording pipettes were pulled to a resistance of 1-3 MΩ with a P-97 horizontal puller (Sutter Instruments), and access resistance—as measured by the instantaneous current response to a-5 mV step with pipette capacitance cancelled—was always less than 8 MΩ. Light-evoked currents were induced using 2 ms full field illumination through the microscope objective at 0.2 Hz using a 4-wavelength high power LED light source (Thorlabs LED4D067, with a DC4100 4-channel LED driver; power measured at objective focal plane was ~1 mW), with the exception of the experiments measuring excitation spectra, in which case a Polychrome V monochromator (TILL Photonics) was used as the light source. Responses were measured with a Multiclamp 700B amplifier (Molecular Devices) and AxoGraph X acquisition software.

Internal Solutions for Whole Cell-Recordings

To evaluate the ionic basis of the light-evoked currents four different internal solutions were used: Cs-Cl, TEA-Cl, Na-Cl and K-Gluc. The Cs-Cl solution contained 5 mM CsCl, 130 mM CeMeSO$_4$, 10 mM HEPES, 0.5 mM EGTA, 0.4 mM Na-GTP, 4 mM Mg-ATP, 10 mM phosphocreatine, and was adjusted to pH 7.3. To replace cations, TEA-Cl containing 140 mM TEA-Cl, 10 mM HEPES, 0.5 mM EGTA, and 10 mM phosphocreatine, adjusted to pH 7.3 was used. K-Gluc solution, in turn, contained 130 mM K-Gluconate, 5 mM KCl, 10 mM HEPES, 0.5 mM EGTA, 0.4 mM Na-GTP, 4 mM Mg-ATP, 10 mM phosphocreatine, adjusted to pH 7.3. Na-Cl based internal solution contained 135 mM NaCl, 3 mM KCl, 1.3 mM $CaCl_2$), 1 mM $MgSO_4$, 10 mM HEPES, 0.4 mM Na-GTP, 4 mM Mg-ATP, 10 mM phosphocreatine.

Ammonium Prepulse Protocol

To address the role of pH in the light-evoked FLInChR current, an ammonium prepulse protocol was used. Briefly, an ammonium challenge was used to shift internal pH basic and then acidic. The normal extracellular solution was first replaced with one in which 20 mM $NH_4Cl$ was added and 20 mM NaCl was omitted. Subsequently, a sodium-free (Na—) extracellular solution containing an equimolar substitution of N-methyl-D-glucamine (NMDG) for NaCl was used to replace the ammonium challenge and used for the rest of the recording session. All solutions contained SR95531 (5 µM) and Kynurenic acid (0.1 mM).

In Vitro Whole-Cell Slice Electrophysiology

Adult (6-8 weeks old) GAD2-IRES-Cre (Jackson Laboratory, Stock #010802) mice were injected with AAV2/1 CAG-FLEX FLInChR-m Venus; sections were taken 3-4 weeks post injection. Mice were deeply anaesthetized under isoflurane, decapitated, and the brains were removed. Coronal midbrain slices (300 µM thick) were sectioned (Leica VT1200S, Germany) in ice-cold modified artificial cerebral spinal fluid (aCSF) (52.5 mM NaCl, 100 mM sucrose, 26 mM $NaHCO_3$, 25 mM glucose, 2.5 mM KCl, 1.25 mM $NaH_2PO_4$, 1 mM $CaCl_2$), 5 mM $MgCl_2$, and 100 µM kynurenic acid). Slices were transferred to a holding chamber and incubated at 35° C. for 30 minutes in modified aCSF (119 mM NaCl, 25 mM $NaHCO_3$, 28 mM glucose, 2.5 mM KCl, 1.25 mM $NaH_2PO_4$, 1.4 mM $CaCl_2$), 1 mM $MgCl_2$, 3 mM sodium pyruvate, 400 µM ascorbate, and 100 µM kynurenic acid, saturated with 95% $O_2$/5% $CO_2$) and then stored at 21° C.

For recordings, slices were transferred to a recording chamber perfused with modified aCSF (119 mM NaCl, 25 mM $NaHCO_3$, 11 mM glucose, 2.5 mM KCl, 1.25 mM $NaH_2PO_4$, 1.4 mM $CaCl_2$), 1 mM $MgCl_2$, 3 mM sodium pyruvate, 400 µM ascorbate, saturated with 95% $O_2$/5% $CO_2$) and maintained at 32-34° C. at a flow rate of 2-3 mL/minute. Substantia nigra GABAergic neurons expressing the opsin were targeted for recordings. Voltage clamp recordings of evoked photocurrents were made using electrodes (5-8 M (2) containing a $CeMeSO_4$-based intracellular solution (in mM) (114 mM $CeMeSO_4$, 4 mM NaCl, 10 mM HEPES, 5 mM QX314.Cl, 0.3 mM GTP, 4 mM ATP, 10 mM phosphocreatine, pH 7.5). Recordings were made using a MultiClamp700B amplifier (Molecular Devices) interfaced to a computer using an analog to digital converter (PCI-6259; National Instruments) controlled by custom written scripts (to be made available at dudmanlab.org/) in Igor Pro (Wavemetrics). Photo-activation was carried out using a dual scan head raster scanning confocal microscope and control software developed by Prairie Systems and incorporated into a BX51 upright microscope (Olympus America). Individual neurons were patched under DIC optics with a water-immersion 40X objective. Cells were held at −70 mV and evoked current measured following brief 1 ms wide field illumination (470 mM or 590 mM). To measure spiking activity, current-clamp recordings were made using a potassium gluconate-based intracellular solution (137.5 mM potassium gluconate, 2.5 mM KCl, 10 mM HEPES, 4 mM NaCl, 0.3 mM GTP, 4 mM ATP, 10 mM phosphocreatine, pH 7.5). Depolarizing current steps (200 ms) were used to evoke high frequency spiking of GABAergic neurons, while brief 100 ms wide field illumination (470 mM, 1 mW at the focal plane of the objective) during the current step was used to assess the effectiveness of FLInChR to suppress evoked spiking. Progressively longer photostimulation was used to assess effect of duration on spiking suppression. Analysis of postsynaptic evoke currents and spiking was performed using custom written analysis code in Igor Pro (Wavemetrics). Rise time constants of postsynaptic currents were measured by finding the 20-80% slope of the rising phase of the stimulus-evoked current. Decay time constant of postsynaptic currents were measured by fitting a single exponential to the decay phase of the stimulus-evoked currents. Spikes were detected at the threshold of maximum acceleration.

In Vivo Perturbation of SNr GABAergic Activity During Effort-Based Operant Task

Adult GAD-IRES-Cre mice were individually housed in a temperature and humidity-controlled room maintained on a reversed 12 hour light/dark cycle. Following 1 week of recovery from surgery for targeted injection of AAV2/1 CAG-FLEX FLInChR-m Venus into SNr and placement of the head fixation chamber, mice were put onto water restriction with water consumption limited to at least 1 mL per day. Mice underwent daily health checks and water restriction was eased if mice fell below 70% of their body weight at the beginning of deprivation.

Water deprived mice were trained on a head-fixed variable amplitude operant task as described elsewhere (see, e.g., Osborne and Dudman, PloS one 9: e89007 (2014); and Panigrahi et al., Cel/162:1418-1430 (2015)), undergoing at least 2 weeks of daily sessions of initial training prior to perturbation experiments. For training, mice were placed in a darkened chamber with both paws positioned on a small metal handle attached to a joystick with two degrees of freedom (as seen in FIG. 9A). Movement of the joystick was detected by a Hall effect sensor with a linear voltage/displacement relationship. Voltage traces for each axis were recorded at 10 kHz and analysis of movements conducted offline. Movement threshold detection and triggering of water delivery were accomplished with a custom micro controller device. A session typically consisted of 120 trials within 7 blocks at different threshold amplitude requirements.

Individual forelimb movements, 'reaches', were extracted from voltage traces by thresholding the change in position and ensuring that movements were separated by at least 200 ms. To extract parameters of the outward component of the reach, a technique was followed as described elsewhere (see, e.g., Gallivan and Chapman, Frontiers in neuroscience 8:215 (2014)). Briefly, the outward component of the reach was determined by finding the end point of maximum displacement. A reach was defined as the trajectory from earliest detectable movement to reaching the maximum displacement (the most eccentric point on the convex hull that captured the trajectory). Movement velocity was computed with summary statistics of the trajectory (max, average).

Photostimulation was delivered via a fiber coupled solid state laser (488 nm; LaserGlow) coupled via a ferrule sleeve to an optical fiber (200 µm diameter) positioned just above the SNr. Laser pulses were gated through the analog modulation circuitry of the laser by modulating the pulse width (1-10 ms). Pulse trains (16.7 Hz; 450 ms duration) were triggered by displacement of the joystick past a threshold lower in magnitude than the threshold required to elicit reward delivery. A randomly chosen 25% of all trial-initiating movements (as detected online) were allowed to trigger photo stimulation.

Behavioral Experiments in C. elegans

For body-wall muscle expression in (. elegans, pmyo-3:: FLInChR:: m Venus was synthesized in a codon optimized manner, resulting in the plasmid pAB15. The respective transgenic strain ZX2282 (zxEx1105 [pmyo-3:: FLInChR:: m Venus; pmyo-2:: CFP] in $N_2$), was generated via microinjection of 50 ng/µL plasmid DNA with 2 ng/µL of the co-injection marker pmyo-2:: CFP. Animals were cultured on NGM plates, seeded with E. coli OP-50 strain, in 6 cm petri dishes. For optogenetic experiments, OP-50 was supplemented with ATR (0.15 µL of stock (100 mM in ethanol) mixed with 300 µL OP-50 bacterial solution).

Video analysis of changes in body length upon light stimulation monitored the evoked effect and provided qualitative information, whether the expressed protein worked as a depolarizer (body contraction) or hyperpolarizer (body relaxation). For behavioral experiments, young adult transgenic animals were cultivated overnight on ATR supplemented plates. To guarantee for an artefact free video analysis, the worms were singled on plain NGM plates prior to the experiments. An Axiovert 40 CFL microscope (Zeiss, Germany) with 10× magnification and a Powershot G9 digital camera (Canon, USA) were used to record the animals' behavior. For photo-stimulation of FLInChR, transgenic animals were challenged by 5 second light pulses (HBO light source, 580 nm, 22 mW/mm), controlled via an Arduino-driven shutter (Sutter Instruments, USA). The body length analysis was performed based on a custom written script for Matlab (Mathworks, USA). For the analysis of data, the animals' body length was normalized to the recording period prior to illumination.

Extracellular Electrophysiological Identification of FLInChR-Expressing Neurons in Awake Rats Extracellular electrophysiology was performed using tetrode microdrives as described elsewhere (see, e.g., Karlsson et al., Science 338:135-139 (2012)) in combination with viral delivery of FLInChR and fiber optic delivery of light. Cortico-striatal neurons in the Anterior Congulate Cortex (Cg1) of adult Long-Evans rats were labeled by combining injections of two viruses. rAAV2-retro-Cre (titer: 7.1 e12 GC/ml) was injected bilaterally into the striatal axonal field (ML: 1.94 mm, AP: 2.29 mm, DV: −4.57 mm; 600 nl per site) with the aim of achieving retrograde access to cortico-striatal neurons. A Cre-dependent FLInChR construct was delivered through localized viral injection in the cortex, ~1.5 mm away from the recording site to minimize damage. To ensure sufficient spread of the virus, rAAV2-retro was chosen as the serotype for delivery, but with the aim of utilizing its enhanced local spread rather than retrograde functionality. rAAV2-retro-CAG-FLEX-FLInChR (titer: 9.2 e12 GC/ml) was thus injected into the dorsal medial prefrontal cortex (ML: −0.6 mm, 0.6 mm AP: 1.2 mm, 1.2 mm DV: −3.0/2.5 mm, −3.0/2.5 mm; 300 nl per site). Several week after virus injection, optical-fiber-containing microdrive was implanted over rostral ACC (ML: −0.6 mm; AP: 2-3 mm)

Light delivery was accomplished using a fiber optic lowered from one of the shuttles of the microdrive, where the fiber optic transmitted light from a laser diode, which was controlled using custom hardware triggered remotely by infrared light and custom software. The fiber optic (200 µm core, 0.5NA hard polymer fiber optics, FP200URT; Thor-Labs), was butt coupled to a laser diode (520 nm; Cat No: PL520_B1; World Star Tech) bonded (Norlands 68).

Fibers were sharpened using chemical etching approach. Specifically, the cable jacket, strengthening fibers, and outer plastic coating (typically white or orange) were fully removed, leaving 1 cm of fiber optic cable and inner plastic coating intact. Then 2 mm of the fiber tip (with final layer of plastic coating still attached) was submerged in 48% hydrofluoric acid topped with mineral oil for 85 min, followed by water for 5 minutes (submerging 5 mm), and acetone for 2 minutes (to soften the plastic). The plastic coating was then gently cut with a razor and pulled off with tweezers to reveal a 1 mm sharp-etched fiber tip. Light emitted from the fiber optic tip was ~ 2 mW, leading to an estimated power density of ~60 mW/mm2. Manufacturing, parts information and detailed documentation are provided online at (karpova-lab.github.io/cerebro/). Light pulses of 20 ms duration were delivered at 0.5 Hz throughout the recording session, in order to inactivate spontaneous and behaviorally evoked activity.

After the electrophysiology experiments, single units were isolated and clustered as described elsewhere (see, e.g., Karlsson et al., Science 338:135-139 (2012)). Peri-event histograms were used to examine the light-dependent inactivation of neuronal activity (FIG. 9I). To discover single units that had light-dependent inactivation, the neuronal activity was z-scored and units were selected that had a decrease of at least two standard deviations for at least 20% of 1 ms time bins during the 20 ms light pulse period. A histogram was constructed of the latency to inactivation of these selected units, where the latency was the time after light onset to the first bin that had an activity decrease of at least two standard deviations (FIG. 9I).

Extracellular Electrophysiological Identification of FLInChR-Expressing Neurons in Awake Rat For cell-type specific in vivo recordings from motor cortex, rAAV2-CAG-Flex-FLInChR-m Venus was injected to the pons bilaterally (relative to lambda: 0.4 mm anterior, 0.4 mm lateral, 5.5, 5.75, 6 mm deep, 70 nL/depth) in Sim1-KJ8 mice, selectively labelling a pyramidal type (PT) layer 5 population. Mice were awake during recordings and were generally immobile, having been previously head restrained for behavioral training. Prior to recordings, a craniotomy was made over the recording site (from bregma: 0.5 mm anterior, 1.7 mm lateral) at least 4 hours prior to recording. Exposed brain tissue was kept moist with phosphate-buffered saline at all times, and craniotomy sites were covered with Kwik-Sil elastomer (WPI) outside of the recording session.

Juxta-cellular recordings were performed as described elsewhere (Coddington and Dudman, bioRxiv, 238881 (2017)). Briefly, a small craniotomy (<200 µm diameter) was made over the recording site (at least 4 hours prior to recording). Exposed brain tissue was kept moist with phosphate-buffered saline at all times, and craniotomy sites were covered with Kwik-Sil elastomer (WPI) outside of the recording session. Borosillicate glass pipettes (Sutter, BF165-120-10) were pulled to a long taper (resistance 5-8 mOhm) with a P-97 micropipette puller (Sutter). Pipettes were filled with 0.5 M NaCl solution and mounted in a holder with a side port (Warner, PE30W-T17P) to allow insertion of a fiber (105 µm core, 0.22 NA, Thorlabs) that was coupled to a 473 nm laser (OEM Laser Systems) to carry light to the pipette tip. Pipettes were lowered through the brain with a micromanipulator (Luigs and Neumann) while a small cycling current injection allowed monitoring of resistance changes across the pipette tip. Within the target region (700-1100 micron from pial surface), the pipette tip was advanced by 1-2 µm steps until a steep increase in resistance was detected. The pipette was then advanced 5-10 µm until positive-going spikes were resolved well above noise (>~0.5 mV). FLInChR expression and responses were assayed with single laser pulses of varying durations (0.5-5 sec), with power measured out of the tip of an exposed pipette of 5 mW. Responses were amplified (Multiclamp 700B, Axon Instruments), then digitally recorded at a 30 kHz sample rate with a Cerebus Signal Processor (Blackrock Microsystems).

For neural population recording using the neuropixel probe, awake mice fully recovered from craniotomy were head-fixed in a RIVETS chamber. A neuropixel probe (option 3 phase A) with 374 recording sites was lowered through the craniotomy manually. After a smooth descent (200 µm/minute), the probe sat still at the target depth for at least 5 minutes before initiation of recording to allow the electrodes to settle. An Ag wire was soldered onto the reference pad of the probe and shorted to ground. This reference wire was connected to an Ag/AgCl wire was positioned on the skull. The craniotomy and the Ag/AgCl wire were covered with a saline bath. Voltage signals are filtered (high-pass above 300 Hz), amplified (200x gain), multiplexed and digitized (25 kHz) on the base, allowing the direct transmission of noise-free digital data from the probe, and were recorded using an open-source software SpikeGLX (github.com/billkarsh/SpikeGLX). Recorded data were pre-processed using an open-source software JRCLUST (github.com/JaneliaSciComp/JRCLUST) to identify single- or multi units in the primary motor cortex (M1). To assay FLInChR expression and responses, a fiber (200 µm core, 0,39 NA, Thorlabs) coupled to a 574 nm laser source (Omicron) was placed to deliver light onto the craniotomy. Single laser pulses of 1-second duration with power measured at the tip of the fiber of 8 mW were delivered 60 times with 8-second intervals.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An inverted transporter polypeptide, said inverted transporter polypeptide comprising:
    a leader sequence comprising a transmembrane domain of an integral membrane protein, wherein the transmembrane domain of the integral membrane protein is selected from a Neurexin 1B transmembrane domain, a synaptobrevin transmembrane domain, and a *Drosophila* olfactory receptor transmembrane domain; and
    a transporter protein comprising an extracellular N-terminus of a light-gated ion channel, wherein the light-gated ion channel is a *Chlamydomonas reinhardtii* rhodopsin;
    wherein said inverted transporter polypeptide presents the extracellular N-terminus of said light-gated ion channel on an intracellular side of a membrane of a cell.

2. The inverted transporter polypeptide of claim 1, wherein said inverted transporter polypeptide inhibits the excitability of said cell.

3. The inverted transporter polypeptide of claim 2, wherein said cell is a neuron or a myocyte.

4. The inverted transporter polypeptide of claim 1, wherein said *Chlamydomonas reinhardtii* rhodopsin is selected from the group consisting of a channelrhodopsin, archaerhodopsin, and halorhodopsin.

5. The inverted transporter polypeptide of claim 4, wherein said transporter protein comprises a channelrhodopsin, and wherein said channelrhodopsin comprises a substitution of the glutamic acid at residue 123 relative to the channelrhodopsin shown in SEQ ID NO: 1 with a threonine (E123T) or a substitution of the threonine at residue 159 relative to the channelrhodopsin shown in SEQ ID NO:1 with a cysteine (T159C).

6. The inverted transporter polypeptide of claim 4, wherein said transporter protein comprises a channelrhodopsin, and wherein said channelrhodopsin comprises a E123T substitution and a T159C substitution relative to the channelrhodopsin shown in SEQ ID NO: 1.

7. The inverted transporter polypeptide of claim 1, wherein said inverted transporter polypeptide comprises a sequence selected from the group consisting of the sequence set forth in SEQ ID NO:5, the sequence set forth in SEQ ID NO:6, and the sequence set forth in SEQ ID NO:7.

8. A method for altering the excitability of a cell, said method comprising:
    providing the inverted transporter polypeptide of claim 1 to the cell, wherein the inverted transporter polypeptide presents the extracellular N-terminus of said light-gated ion channel on an intracellular side of a membrane of said cell, wherein the inverted transporter polypeptide alters the excitability of the cell.

* * * * *